(12) United States Patent
Naleway et al.

(10) Patent No.: US 8,916,346 B2
(45) Date of Patent: Dec. 23, 2014

(54) REAGENTS AND METHODS FOR DIRECT LABELING OF NUCLEOTIDES

(75) Inventors: John J. Naleway, Eugene, OR (US); Ying Jiang, Eugene, OR (US); Ryan Link-Cole, Monmouth, OR (US)

(73) Assignee: Marker Gene Technology, Inc., Eugene, OR (US)

( * ) Notice: Subject to any disclaimer, the term of this patent is extended or adjusted under 35 U.S.C. 154(b) by 0 days.

(21) Appl. No.: 13/373,959

(22) Filed: Dec. 6, 2011

(65) Prior Publication Data

US 2013/0150254 A1 Jun. 13, 2013

Related U.S. Application Data

(60) Provisional application No. 61/459,225, filed on Dec. 9, 2010.

(51) Int. Cl.
| | | |
|---|---|---|
| *C12Q 1/68* | (2006.01) | |
| *C07D 209/24* | (2006.01) | |
| *C07D 471/04* | (2006.01) | |
| *C07D 495/04* | (2006.01) | |
| *C07J 19/00* | (2006.01) | |
| *C07D 311/16* | (2006.01) | |
| *C07D 219/14* | (2006.01) | |
| *C07D 271/12* | (2006.01) | |
| *C07D 471/06* | (2006.01) | |
| *C07D 403/06* | (2006.01) | |

(52) U.S. Cl.
CPC ............ *C12Q 1/6841* (2013.01); *C07D 471/04* (2013.01); *C07D 495/04* (2013.01); *C07J 19/00* (2013.01); *C07D 209/24* (2013.01); *C07D 311/16* (2013.01); *C07D 219/14* (2013.01); *C07D 271/12* (2013.01); *C07D 471/06* (2013.01); *C07D 403/06* (2013.01)
USPC ......... 435/6.1; 435/6.11; 548/455; 536/25.32

(58) Field of Classification Search
None
See application file for complete search history.

(56) References Cited

U.S. PATENT DOCUMENTS

2003/0186448 A1* 10/2003 Bourget et al. ................. 436/56

OTHER PUBLICATIONS

Aggarwal et al., "Catalytic Asymmetric Synthesis of Epoxides from Aldehydes Using Sulfur Ylides with In Situ Generation of Diazocompounds," Angew. Chem. Int. Ed. 2001, 40:1430-1433.*
Creary, "Tosylhydrazone salt pyrolyses: Phenyldiazomethanes," Organic Syntheses 1990, Wiley: N.Y., Coll. vol. 7, p. 438-443.*
Artaud et al., "Polymer Supported Alkoxides: Synthesis and Reactivity," J. Chem. Soc. 1985, Perkin Trans. 1, 1257-1260.*
Nam et al., "Reactions of Solid-Supported Reagents and Solid Supports with Alcohols and Phenols through Their Hydroxyl Functional Group," J. Comb. Chem. 2003, 5:479-546.*

* cited by examiner

*Primary Examiner* — Samuel Woolwine
*Assistant Examiner* — Kaijiang Zhang
(74) *Attorney, Agent, or Firm* — Timothy L. McCutcheon

(57) ABSTRACT

The present invention provides systems and methods for production of activatable diazo-derivatives for use in labeling nucleotides. Labeling nucleotides is accomplished by contacting a stable hydrazide derivative of a detectable moiety with an activating polymer reagent which is used to directly label the nucleotide sample. Labeling occurs on the phosphate backbone of the nucleotide which does not perturb hybridization of the labeled nucleotide with its anti-sense strand. Since the method involves direct labeling, all types of nucleotides can be labeled without prior amplification or alteration.

1 Claim, 2 Drawing Sheets

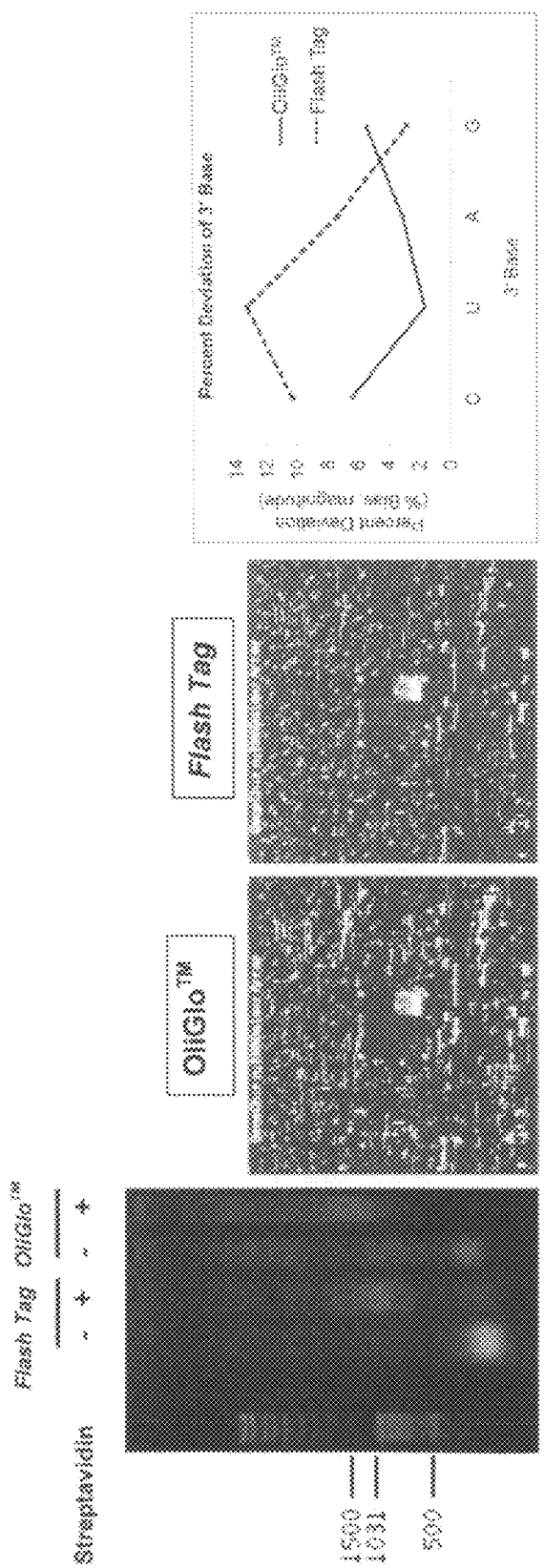
Figure1: Labeling of miRNA with OliGlo™ biotin probe, application in miRNA array analysis and comparison of 3' Base bias for probe labeling.

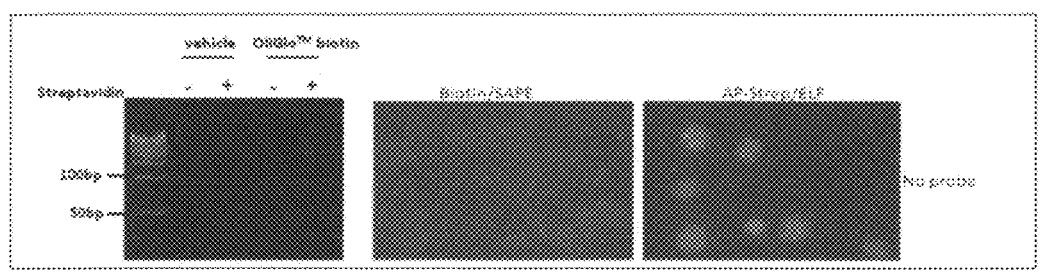
Figure 2. OliGlo™ biotin labeled *lacZ* probe in mRNA in situ hybridization.

REAGENTS AND METHODS FOR DIRECT LABELING OF NUCLEOTIDES

CROSS-REFERENCE TO RELATED APPLICATIONS

The present application claims priority in U.S. Provisional Application Ser. No. 61/459,225, filed Dec. 9, 2010.

FIELD OF THE INVENTION

The present invention relates to methods and systems for labeling nucleotides using in situ prepared reactive compounds that create stable phosphodiester and phosphotriester linkages between reporter molecules (fluorescent, chemiluminescent, receptor ligand or chromogenic compounds) and internal or terminal phosphate moieties of nucleotides, oligonucleotides or genomic DNA or RNA samples.

BACKGROUND OF THE INVENTION

A number of agents have been described for labeling nucleic acids, whether probe or target, for facilitating detection of target nucleic acid. Suitable labels may provide signals detectable by fluorescence, radioactivity, colorimetry, X-ray diffraction or absorption, magnetism or enzymatic activity, and include, for example, fluorophores, chromophores, chemiluminescent compounds, radioactive isotopes, enzymes, and ligands having specific binding partners.

Fluorescent dyes are particularly suitable for detecting nucleic acids. The use of fluorescence labeled polynucleotide probes and polynucleotide hybridization assays have been widely reported. These methods typically require purified DNA or RNA samples for labeling. Other uses of fluorescent dye labeling have been in the field of separation and isolation or purification of nucleic acids from complex biological or clinical specimens.

Typical nucleic acid assays comprise several steps that include target isolation, enzymatic amplification, incorporation of reactive or labeled nucleotides during amplification, purification and detection by hybridization onto specific complementary probe(s). The analysis of target/probe hybridization is the key step in this process and requires the use of fluorescent molecules to specifically label the target nucleic acids. These labels are incorporated into the target DNA or RNA either during enzymatic amplification or post-amplification 5-end enzymatic incorporation of a single fluorescently or biotin-labeled dideoxy-nucleotide.

It is essential that the labeling method not perturb base-pairing hybridization critical for preserving assay specificity. Nevertheless, labeling by enzymatic incorporation often leads to interference with the subsequent hybridization detection step, because current fluorescent labels are attached to the base (purine, pyrimidine) portion of the nucleotides, where base-pairing and hybridization occurs. In addition, enzymatic labeling methods make use of additional enzymatic steps, which require precise calibration to achieve a reproducible labeling yield. Moreover, because the enzymes used depend on the target type (DNA or RNA) and sequence, no specific method is universally applicable to all nucleic acids, and sequence perturbation is often observed.

To remedy this, methods of direct labeling have been used with varying degrees of success, including reactive Cy3 or Cy5-NHS esters, dye amidites or iodoacetamido or bromomethyl dyes. In addition, photobiotin, biotin or digoxigenin-dUTP probes and chemiluminescent detection, fluorescent dendrimer labeling pyrene labeling, as well as radiolabeling methods have been described, but all of these methods suffer from either cumbersome procedures, or are unamenable to direct labeling and hybridization assays using a variety of samples and methods.

Systems for labeling DNA or RNA samples through their phosphate groups have been described in the prior art, however, these methods suffer from obvious problems in the preparation of the active labeling compounds, their solubility, stability as well as their reproducibility in labeling applications. Current methods of preparing active diazomethyl derivatives (hydrazine, $MnO_2$) also involve messy and toxic reagents that are not amenable to biological laboratory use.

The present invention alleviates these difficulties by preparing active diazo labeling reagents in situ, from stable precursor molecules derived from a variety of highly fluorescent dyes and other detection labels. In addition, the present invention defines simple and highly effective methods of activation of the precursor molecules using either highly basic or polymer based reagents, that provide a shelf life of more than six months and are convenient for end-user applications. The systems described in the present invention provide a convenient method for use by biologists and clinicians to label or monitor genomic DNA or RNA samples, nucleotides or oligonucleotides for easy detection and quantification using modern instrumentation and detection systems.

We therefore propose a direct labeling methodology that reduces hybridization and sequence specificity effects by direct (terminal and backbone) phosphate labeling.

SUMMARY OF THE INVENTION

The present invention relates to reagents, methods and systems for in situ preparation of reactive labeling compounds from stable precursor molecules and use of these reagents for efficient labeling of nucleotides, oligonucleotides or genomic DNA or RNA samples with reporter molecules including, but not limited to, fluorescent, chemiluminescent, receptor ligand or chromogenic compounds. The labeling agents and methods described are also useful for a variety of additional applications, involving analysis of phosphorylated proteins, phospholipids, as well as carboxy or sulfonated analytes.

BRIEF DESCRIPTION OF THE DRAWINGS

FIG. 1. Demonstrates the labeling of miRNA using compounds of the present invention and application in miRNA array analysis.

FIG. 2 Demonstrates in situ labeling of mRNA using compounds of the present invention.

DETAILED DESCRIPTION OF THE INVENTION

The unique advantages of the present invention relates to the direct labeling approach. Direct labeling has unique advantages over existing methods including improved detection limits (multiple labelings/nucleotide fragment), improved photostability, sequence insensitivity (due to labeling on the phosphate backbone), improved quantification, elimination of the complex and critical step of reverse transcription of mRNA into cDNA, quickness and ease of assay and minimal hybridization perturbation effects. Since the method does not require enzymatic replication step(s), the resulting labeled DNA or RNA can be used for ultrasensitive hybridizations which represent the original sample without any enzymatic replication or label incorporation biases that current techniques experience.

One embodiment of the invention is directed to reactive agents comprising a detectable moiety bonded to a phosphate reactive moiety wherein the phosphate reactive moiety contains at least one group capable of covalently bonding to an analyte to form a stable conjugate that can be selectively identified and quantitated. Detectable moieties will have a selectively detectable physical property such as fluorescence, absorption, color, light emission (chemiluminescence), radioactivity or an ability to specifically bind to a coupling agent such as avidin or streptavidin, antibodies, antigens or other binding proteins. The phosphate reactive moiety should be capable of forming one or more covalent bonds with a chemical group on the DNA, RNA, oligonucleotide, oligodeoxynucleotide, or other phosphate, sulfate, carboxylic acid, sulfonic acid or similar analyte. Those covalent bonds will not be cleaved or photocleaved with the electromagnetic radiation releasing the substrate.

Among the most efficient and reactive reagents for covalent attachment to the phosphate groups of oligonucleotides, RNA and DNA are diazomethyl derivatives. But these compounds are extremely reactive and unstable, especially in aqueous solutions which are required for oligonucletide, DNA and RNA solubility. Substituted aryldiazomethyl derivatives have been utilized for this purpose but their reactivity is limited by both poor stability and cumbersome methods of preparation utilizing toxic reagents and poor yielding results ($MnO_2$ and hydrazine). In addition, the reactive diazomethyl derivatives are difficult to purify and utilize in common biological settings.

The present invention employs stable arylsulfonylhydrazides (e.g. triisopropylsulfonylhydrazides, benzenesulfonylhydrazides or toluenesulfonylhydrazides) as precursors for simple and efficient production of the active diazomethyl reactive labeling reagents. These stable precursors are especially useful for application to the oligonucleotide, DNA or RNA labeling field, where such stable intermediates are of great use for biological applications.

Arylsulfonylhydrazides have been previously described for protection of hydrazide derivatives and synthesis of diazo compounds. However, strongly basic conditions (KOH/MeOH:THF or NaOMe/MeOH) are required to produce the final diazomethyl compounds from the arylsulfonylhydrazide precursors. In addition, the active diazo compounds could only be isolated by cumbersome extraction techniques, evaporation and drying steps and final dissolution in a suitable co-solvent for an eventual labeling reaction.

Although the present invention can utilize these highly basic methods of preparation of the diazomethyl labeling reagents, we also have developed an efficient set of polymer-based reagents that can be utilized to carry out the same transformation to the active diazo derivatives from the stable precursors, without the need for the extractions, purification, and redissolving steps. This method has been found to both improve the yield of active diazomethyl compounds, and also provide cleaner and more stable reagent samples.

In addition, the method is quick and easy, involving the addition of a solution of the arysulfonylhydrazide precursor in a suitable solvent (such as dry DMF) to a vial containing the polymer-based basic resin, incubating for a period of time at room temperature, and then simply decanting or pipetting the active labeling reagent from the supernatant of this vial for labeling DNA or RNA samples, oligonucleotides or nucleotides, since the polymer-based activating reagent settles to the bottom of the vial on standing. As described below, this quick and efficient labeling system has been found to have utility in a number of significant biological assays.

In a particular embodiment of the invention, the labeling agent has a chemical structure as follows:

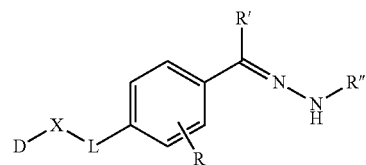

where:
1. R may be an alkyl, aryl, fused aryl, $NH_2$, $CH_2$-halogen, —CN, =O, —S—S—$R_1$, —OH, —$OR_1$, —$CF_3$, —$NO_2$, —CN, —$COOR_2$, —$OP(OR_3)_3$, $N(R_4)R_5$ and —OCO—$R_2$;
2. R' may be hydrogen, alkyl, aryl or substituted aryl;
3. R" may be alkylsulfonyl, arylsulfonyl or substituted alkyl or arylsulfonyl systems;
4. X may be alkyl, substituted alkyl, aryl, substituted aryl, —$CH_2$, O-esters, N-amides, sulfonamide, urea, thiourea, thioether, maleimidothioether, chlorotriazinylamino or other linking groups;
5. R.sub.1, R.sub.2, R.sub.3, R.sub.4 and R.sub.5 may be hydrogen, alkyls, substituted alkyls, aryls or substituted aryls, and may be the same or different;
6. L is a linking arm of one or more polyatomic groups V sub m1 and Q sub m2 which may be the same or different; where V includes one or more optional monoatomic groups which may be the same or different;
7. Q is an optional spacer moiety; and m1 and m2 are integers from 0-8 and may be the same or different; and
8. D is a detectable moiety which is distinct from R.sub.1-R.sub.5 or R".

The reactive labeling agent may also have a general chemical structure:

D-CR'=N—NH—R"

where D is a detectable moiety, which is directly attached to a suitably protected hydrazide group, where the hydrazide function is attached to an aromatic portion of D, such that the carbon of —CR=N—N is a benzylic carbon.

In one embodiment of the invention, the detectable moiety is a chemical group, structure or compound that possesses a specifically identifiable physical property which can be distinguished from the physical properties of other chemicals present in a heterologous mixture. Fluorescence, phosphorescence and luminescence including electroluminescence, chemiluminescence and bioluminescence are all detectable physical properties not found in most substances, but known to occur or to be inducible in others. For example, reactive derivatives of dansyl, coumarins, rhodamine and fluorescein are all inherently fluorescent when excited with light of a specific wavelength and these detection agents can be specifically bound or attached to analyte substances using the present methods. Coumarin has a high fluorescent quantum yield, higher than even a dansyl moiety, and facilitates detection where very low levels of target are being sought. Coumarins are structurally similar to tryptophan, which can be useful, for example in the translation of nascent proteins with non-native amino acids. Fluoresceins have a higher extinction coefficient than coumarins and are compatible with many laser systems for detection. Long wavelength fluorophores such as the rhodamines, carbocyanines, phycocyanines, BODIPY's or quantum dots, in addition, have the added property of analysis in areas of the spectrum distinct from endogenous absorption or fluorescence by biological components of the analyte specimen. It may also be useful to combine certain detectable moieties to facilitate detection or isolation, by either quenching (with a match quenching dye when the analyte is in contact) or by using fluorescence polarization, or fluorescence resonance energy transfer (FRET) systems, where the fluorescence emission of one fluorophore is matched to the absorption of a second fluorophore, and when the two analytes are in physical proximity, the second fluorophore will emit specific wavelengths of light.

As such, one embodiment of the present invention the detectable moiety may be any of a dye, radioisotope, fluorescent compound, chemiluminescent reporter molecule, antibody, antibody fragment, hapten, biotin, derivative of biotin, photobiotin, iminobiotin, digoxigenin, avidin, streptavidin, a lectin, enzyme, acridinium, sugar, apoenzyme, homopolymeric oligonucleotide, hormone, ferromagnetic moiety, paramagnetic moiety, diamagnetic moiety, phosphorescent moiety, luminescent moiety, electrochemiluminescent moiety, chromatic moiety, moiety having a detectable electron spin resonance, electrical capacitance, dielectric constant, electrical conductivity, and combinations thereof.

One embodiment of the present invention is for the detectable moiety to be a fluorescent compound. Fluorescent compounds suitable for use in the present invention include but are not limited to those listed below, all of which are commercially available.

Fluorescent Labeling Compounds 4-acetamido-4'-isothiocyanatostilbene-2-2'-disulfonic acid
Acridine orange
7-amino-4-methylcoumarin (AMC)
7-amino-4-methylcoumarin-3-acetic acid (COUM)
aminonaphthalene trisulfonic acid (ANTS)
7-amino-4-trifluoromethylcoumarin
N-(4-anilino-1-naphthyl)maleimide   4',6-diamidino-2-phenylindole (DAPI)
7H-benz[de]benzimidazo[2,1-a]isoquinoline-7-one
5'-carboxyfluorescein (5-FAM),
5(6)-carboxyfluorescein
5(6)-cathoxyfluorescein, N-hydroxysuccinimide ester (5-FAM-NHS, 6-FAM-NHS)
6-carboxytetramethylrhodamine, NHS ester (6-TAMRA),
6-carboxy-X-rhodamine (ROX)
3-carboxyumbelliferone
4',5'-dichloro-2',7'-dimethoxy-6-carboxyfluorescein (JOE)
5-(4,6-dichlorotriazin-2-yl)aminofluorescein (DTAF)
4,4'-diisothiocyanatostilbene-2,2'-disulfonic acid
7-diethylamino-3-carboxycoumarin
ethylenediamine 1,5-naphthalene sulfonic acid (EDANS)
tetramethylrhodamine isothiocyanate (TRITC)
5(6)-carboxytetramethylrhodamine (TAMRA)
quinolizino fluorescein isothiocyanate (QFITC)
dansyl chloride
eosin isothiocyanate
erythrosin B
fluorescamine (5-aminofluorescein, 6-aminofluorescein)
fluorescein derivatives
4-methylumbelliferone o-phthaldialdehyde
pyrene carboxaldehyde
rhodamine B
rhodamine B derivatives
rhodamine 6G
rhodamine 123
sulforhodamine B
sulforhodamine 101
sulforhodamine 101, acid chloride (Texas Red)

Another embodiment of the present invention is for the detectable moiety to be a luminescent compound, i.e. either chemiluminescent, phosphorescent or bioluminescent. Compounds suitable for use in the present invention include but are not limited to those listed below, all of which are commercially available.

Luminescent Labeling Compounds

Luminol
Isoluminol
Cyalume
$Ru(bipy)_3^{2+}$
D-luciferin (with luciferase activity)
tetrakis(dimethylamino)ethylene (TMAE)
1,2,3-trihydroxibenzene (pyrogallol)
Lucigenin
Coelenterazine
1-Anthryl Schiff's Base
2-Anthryl Schiff's Base
N-(4-Aminobutyl)-N-ethylisoluminol
6-(4-Methoxyphenyl)-2-methyl-3,7-dihydroimidazo[1,2-a]pyrazin-3(7H)-one
2-Methyl-6-phenyl-3,7-dihydroimidazo[1,2-a]pyrazin-3(7H)-one
meso-Tetraphenyl-tetrabenzoporphorine Palladium
4-Aminophthalhydrazide monohydrate
Bis(2-carbopentyloxy-3,5,6-trichlorophenyl)oxalate
9,10-Bis(phenylethynyl)anthracene
5,12-Bis(phenylethynyl)naphthacene
2-Chloro-9,10-bis(phenylethynyl)anthracene
1,8-Dichloro-9,10-bis(phenylethynyl)anthracene
Lucifer Yellow CH
Lucifer yellow VS
2,4,5-Triphenylmidazole
9,10-Diphenylanthracene
Rubrene
Phosphorescent pigments Another embodiment of the present invention is for the detectable moiety to be a chromogenic compound, having either detectable color by visual inspection, or a specific absorption wavelength that can be detected using an infrared, ultraviolet or visible spectrometer. Compounds suitable for use in the present invention include but are not limited to those listed below, all of which are commercially available.

| Chromogenic Labeling Compounds |
| --- |
| 1,4-Phenylenediamine |
| 2,3,5-Triphenyltetrazolium chloride |
| 2,4-Dinitro-5-fluoroaniline |
| 2-Naphthol (beta) |
| 3,3'-Diaminobenzidine |
| 4-Chloro-1-naphthol |
| Acridine Orange |
| Alcian Blue 8GX |
| Alizarin |
| Alizarin Red S |
| Alkali Blue 4 B |
| Aminoeosin |
| Auramine O |
| Azocarmine B |
| Azocarmine G |
| Azophloxine |
| Azure A |
| Azure B |
| Azure II |
| Azure II-Eosin |
| Bengal Rose B |

| Chromogenic Labeling Compounds | Chromogenic Labeling Compounds |
|---|---|
| Benzopurpurine 4B | Nigrosin B |
| Prussian Blue | Nigrosin |
| Bismarck Brown Y (G) | Nile Blue A |
| Bismarck Brown R | Nile Blue |
| Brilliant Green | Ninhydrin |
| Brilliant Cresyl Blue | Nitrazine Yellow |
| Bromocresol Green | o-Nitrophenol |
| Bromocresol Purple | p-nitrophenol |
| Bromophenol Blue | Nitrotetrazolium Blue |
| Bromosulfalein | Orange G |
| Bromothymol Blue | Orcein |
| Carmine | Parafuchsin |
| Carminic acid | Phenosafranine |
| Celestine Blue | Phthalocyanine |
| Quinoline Yellow | Pinacyanol iodide |
| Chlorazol Black | Ponceau BS |
| Chrysoidine G | Ponceau S |
| Cyanosine | Pyronine Y (G) |
| Direct Red | Resorufin |
| Direct Red 80 | Rhodamine B |
| Fast Blue B Salt | Ruthenium Red |
| Fast Blue BB Salt | Safranin T |
| Fast Blue RR Salt | Scarlet R |
| Fast Green FCF | Sirius Rose BB |
| Fast Red 3 GL Salt | Sudan Blue II |
| Fast Red RC Salt | Sudan Orange G |
| Fast Violet B Salt | Sudan Red B |
| Eosin | Sudan Black B |
| Eosin Scarlet | Sulforhodamine B |
| Eriochrome Red B | Tartrazine |
| Erythrosin | Tetranitroblue tetrazolium chloride |
| Ethyl Violet | Tetrazolium Blue chloride |
| Evans Blue Fluka | Tetrazolium Violet |
| Fat Red Bluish | Thiazole Yellow G |
| Fat Black | Thiazolyl Blue |
| Fuchsin | Tetrazolium bromide |
| Gallocyanine | Thiocarbohydrazide |
| Gentian Violet | Thioflavine T |
| Hemalaun | Thionine acetate |
| Hematein | Toluidine Blue |
| Hematoxylin | Tropaeolin 000 No. 1 |
| Hesperidin | Tropaeolin 000 No. 2 |
| Indigocarmine | Trypan Blue |
| Iodonitrotetrazolium chloride | Variamine Blue B salt |
| Janus Green B | Victoria Blue B |
| Nuclear Fast Red | Water Blue |
| 2-chloro-4-nitrophenol | Wright Stain |
| Congo Red | Xylenecyanol FF |
| Cresol Red | |
| Cresyl Violet | |
| Lactophenol Blue | |
| Light Green SF Yellowish | |
| Lipid Crimson | |
| Lugol Solution | |
| Malachite green oxalate | |
| Metanil Yellow | |
| Methylene Blue | |
| Methyl Green | |
| Methyl Orange | |
| Methyl Violet | |
| Morin | |
| Mucicarmine | |
| N-(4-Amino-2,5-diethoxyphenyl)benzamide | |
| N,N-Dimethylaniline | |
| N,N-Dimethyl-p-toluidine | |
| Naphthol AS | |
| Naphthol AS-BI | |
| Naphthol AS-BS | |
| Naphthol AS-D | |
| Naphthol AS-E | |
| Naphthol AS-MX, | |
| Naphthol Blue Black | |
| Naphthol Yellow S | |
| Naphthol Green B | |
| Neotetrazolium chloride | |
| Neutral Red | |

Another embodiment of the present invention is for the detectable moiety to be a protein or enzyme wherein the detectable signal can be amplified by addition of a suitable substrate which can be detected by enzymatic action.

Another embodiment of the present invention is for the detectable moiety to be a hapten or ligand such that the presence of the hapten or ligand can be detected by binding to its specific protein or binding compound. The ligand/anti-ligand or hapten/binding protein pairs will be well known to those skilled in the art and include, for example, biotin-avidin, biotin-streptavidin, hapten-antibody, antigen-antibody, peptide-antibody, sugar-lectin, polynucleotide-sequence complementary to the polynucleotide or other such systems. Often in such cases, the protein, antibody, lectin or other binding moiety is itself labeled with a detection reagent. The protein, antibody, lectin or other binding moiety may also be covalently attached to an additional reagent used to further amplify the detectable signal, by use of, for example, an enzyme activity and appropriate substrate turnover, which releases a separate detectable moiety. Such sandwich type assays are common in Enzyme-Linked Immuno-Sorbent Assay (ELISA) systems.

Another embodiment of the present invention includes a linking group having less than twenty carbon atoms, which may be branched or non-branched. In a particular embodiment the linking group includes four carbon atoms and one heteroatom where the heteroatom may be oxygen or nitrogen. In another embodiment, the linking group is an oligolysine, a polylysine or polyethyleneglycol.

Suitable analytes which can be covalently labeled include phosphorylated proteins, peptides, amino acids, amino acid analogs, nucleic acids, nucleosides, and nucleotides. In addition, phospholipids, vesicles, detergent micelles, cells, virus particles, fatty acids, saccharides containing phosphates or carboxyl groups, polysaccharides having these acid functions, as well as inorganic molecules, metals, and derivatives and combinations thereof will be suitable analytes using these techniques. The analytes may also be pharmaceutical agents such as cytokines, immune system modulators, agents of the hematopoietic system, chemotherapeutic agents, radio-isotopes, antigens, anti-neoplastic agents, recombinant proteins, enzymes, PCR products, receptors, hormones, vaccines, haptens, toxins, antibiotics, nascent proteins, cells, synthetic pharmaceuticals and derivatives and combinations thereof.

Another embodiment of the invention is directed toward methods for converting stable sulfonylhydrazones to the phosphate reactive labeling compounds by use of a solution or polymer based reagent consisting of a solid supported basic or thiol containing derivative. Some of the preferred solid supports for the base include but are not limited to those listed in the table below, all of which are commercially available.

| Polymer Based Solid Supports | |
|---|---|
| Dowex Marathon 550A (OH) | Dowex Marathon A |
| Dowex Marathon MSA | Dowex Marathon 11 |
| Dowex Upcore Mono A-500 | Dowex SBR-P |
| Dowex Monosphere 550A (OH) | Dowex Upcore Mono A-625 |
| Dowex SBR-P C | Dowex SBR-C |
| Dowex MSA-1 C | Dowex Monosphere 550A UPW (OH) |
| Dowex Monosphere 550 LG NG (OH) | Dowex Monosphere 700A (OH) |
| Dowex Monosphere 725A (OH) | Dowex 1 |
| Dowex 21K 16/20 | Dowex 21K 16/30 |
| Dowex 21K XLT | Dowex RPU |
| Dowex TAN-1 | Dowex Marathon A2 |
| Dowex 22 | Dowex Upcore Mono A2-500 |
| Dowex MSA-2 | Dowex SAR |
| Amberlite FPA40 Cl | Amberlite FPA91 Cl |
| Amberlite FPA90 Cl | Amberlite FPA98 Cl |
| Phenol, polymer bound | Rink acid resin |
| (Hydroxymethyl)polystyrene | 4-Benzyl alcohol, polymer bound |
| 4-Benzyloxybenzyl alcohol, polymer bound (Wang Resin) | |
| Thiol-Terminated Polystyrene | |

One embodiment of the present invention is for the direct labeling of an analyte. Such methods are accomplished by contacting a protected labeling compound of the present invention with an activating reagent in situ to generate a reactive labeling compound which then reacts with an analyte having a nucleophilic group capable of reacting with the reactive labeling compound. Suitable analytes include phosphates, carboxylic acids, boronates, nucleotides, deoxynucleotides, oligonucleotides and oligodeoxynucleotides. Particularly suitable analytes are nucleotides, deoxynucleotides, oligonucleotides or oligodeoxynucleotides having a nucleotide base of adenine, thymidine, cytosine, guanine, uridine, purine and pyrimidine which is a constituent of a DNA or RNA polynucleotide. Particularly suitable nucleophilic groups include a phosphate group, a phosphoester, a carboxyl group and a thiolate group.

In a particular embodiment of the invention, the activating reagent is a polymer-based, amino, thiol, dialkylamino, alkoxy or aryloxy compound. In another particular embodiment, the activating reagent has the structure:

R-L-O⁻Alk⁺: wherein

R is a polymeric support for an alkyl or aryl group,
L is a linking arm,
and Alk+ is an alkali metal salt selected from the group consisting of Li+, Na+, K+, and Cs+.

In another particular embodiment, the activating reagent has the structure:

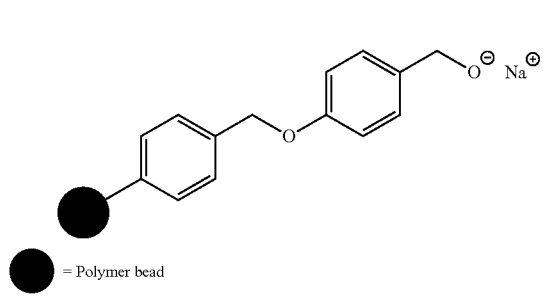 [SMILES: Cc1ccc(COc2ccc(C[O-])cc2)cc1 ; [Na+]]

● = Polymer bead

Another embodiment of the invention is directed to methods for isolating analyte targets from a heterologous mixture without prior purification or with minimal purification. A conjugate is created comprising the reactive labeling agent coupled to an analyte by a covalent bond, wherein said conjugate is comprised of a detectable moiety and the analyte precursor of the target. The conjugate is contacted with the heterologous mixture of analyte hybridization compounds (DNA microarray, hapten binding protein, immobilized antibody or other analysis system) and the target conjugate isolated. This method is useful for the detection and isolation of nascent proteins, nucleic acids and other biological substances.

Another embodiment of the invention is directed to methods for isolating target cells from a heterologous mixture. A conjugate is created comprising the reactive labeling agent coupled to a cell receptor by a covalent bond. The coupled conjugated cell is separated from the mixture of cells using the detection agents' properties of fluorescence, chemiluminescence, color magnetism, or other detection method. Target cells are then easily isolated by such techniques as fluorescence activated cell sorting in an automated fashion.

Another embodiment of the invention is directed to pharmaceutical compositions comprising the use of the reactive labeling reagent with a pharmaceutical compound and with a pharmaceutically acceptable carrier such as water, an oil, a lipid, a saccharide, a polysaccharide, a glycerol, a collagen or a combination thereof. Such labeled pharmaceuticals may be used in the detection, prophylaxis and treatments of diseases and disorders in humans and other mammals.

Another embodiment of the invention is directed to target molecules isolated by the above methods which may be used in pharmaceutical compositions or other compositions and mixtures for industrial applications, for example in determination of the half-life of pharmaceutical compositions in vivo.

The following examples are provided as illustrations of the methods and reagents that can be used for these purposes. Other advantages and embodiments of the invention will become clear from the following examples.

Example 1

Preparation of 4-(2-aminoethyl)benzaldehyde hydrochloride (M0748)

The common precursor for the preparation of stable hydrazide dyes is 4-(2-aminoethyl)benzaldehyde hydrochloride. This aldehyde is prepared through conversion of 4-(2-aminoethyl)benzyl alcohol to the corresponding trifluoroacetamide (ethyl trifluoroacetate, diisopropylethyl amine, THF) followed by Swern oxidation and deprotection (HCl, water/methanol, reflux). Briefly, methyl-(4-alpha-bromomethyl) benzoate (15.85 g, 69.2 mmole) was dissolved in warm methanol (50 mL), cooled to room temperature and a solution of potassium cyanide (7.18 g, 120 mmole) in water (13 mL) added slowly with stirring, in the absence of heating. The exothermic reaction was cooled to room temperature, and allowed to react for 14 hours. The methanol was removed by vacuum distillation (rotovap) and the remaining aqueous solution extracted with diethylether (2×25 mL). The combined ether layers were washed with water (3×50 mL) and brine (1×50 mL), dried over anhydrous sodium sulfate, and evaporated to a brown solid which was applied to a column of silicagel 60 (70-230 mesh, 4×40 cm) and eluted with dichloromethane. Fractions containing the purest product bands of methyl 4-cyanomethylbenzoate were combined, evaporated and dried in vacuo to a colorless solid (M0731: 6.0 g, 50%).

A sample of M0731 (4.00 grams, 22.8 mmole) was dissolved in anhydrous tetrahydrofuran (20 mL) under dry $N_2$ gas and 1 M $BH_3$/THF (0.097 mL, 97 mmole, 4.25 equiv.) added slowly with stirring. The reaction was heated to reflux for 9 hours, cooled and conc. HCl (7.8 mL) added dropwise to neutralize the $BH_3$. The solvent was removed by rotary evaporation, and the gummy solid triturated with water (25 mL) and $CHCl_3$ (75 mL). The chloroform layer was removed, and the aqueous layer adjusted to pH 12 with 10N NaOH solution, and extracted with $CHCl_3$ (3×75 mL). The chloroform solution was filtered and the solvent removed to give an oil that crystallized on drying overnight in vacuo to give the 4-hydroxymethylphenethylamine (M0733: 1.85 g, 54%). $^1$H-NMR (CDCl$_3$) δ: 7.3 (t, 2H, aromatic); 7.2 (d, 2H, aromatic); 4.6 (s, 2H, benzylic); 2.9 (t, 2H); 2.8 (t, 2H).

A sample of M0733 (250 mg, 1.65 mmole) was treated with ethyltrifluoroacetate (214 uL, 1.80 mmole) in dry THF (2 mL) under dry $N_2$ gas and this mixture allowed to stir at room temperature for 30 min. until TLC (9:1 $CH_2Cl_2$:MeOH) indicated complete conversion to a new higher $R_f$ product. The reaction mixture was diluted with $CH_2Cl_2$ (5 mL) washed with water (1×10 mL), dilute 5% HCl solution (1×10 mL) and water (1×10 mL), filtered through a cotton plug, and the solvent removed to give the trifluoroacetamide (M0735: 344 mg, 83%).

A solution of DMSO (305 μL, 4.30 mmole) in $CH_2CL_2$ (2 mL) was cooled to −78° C. (dry ice/acetone bath) and trifluoroaceticanhydride (589 uL, 4.17 mmole) added dropwise followed by a sample of M0735 (344 mg, 1.39 mmole) dissolved in $CH_2Cl_2$ (2.5 mL) added dropwise. This mixture was stirred at −78° C. for 2 hours and Hünig's base (diisopropylethylamine) added (1.31 mL, 7.5 mmole) added. The reaction was allowed to continue stirring at −78° C. for 3 hours and then at room temperature overnight. The reaction mixture was washed with dilute HCl solution (2×10 mL) and water (3×10 mL), filtered through a cotton plug and the solvent removed to give a white solid (M0736: 377 mg, 110%) which contained traces of DMSO by NMR analysis. Further purification by silicagel 60 column chromatography (2×20 cm) with elution using $CH_2Cl_2$ followed by 2% EtOAc in $CH_2Cl_2$ gave an analytical sample (M0736: 114 mg, 33%). $^1$H-NMR (CDCl$_3$) δ: 10.0 (s, 1H, CHO); 7.8 (dd, 2H, aromatic); 7.4 (d, 2H); 6.5 (br s, 1H); 3.7 (m, 2H); 3.0 (t, 2H).

The sample of M0736 (114 mg, 465 μmol) was treated with anhydrous 1N HCl/MeOH (10 mL) and this mixture heated to reflux overnight. After cooling to room temperature, the solvent was removed, by rotary evaporation, and the crude product triturated with diethyl ether and dried in vacuo to give an off-white solid, 4-(2-aminoethyl)benzaldehyde hydrochloride (M0748: 81 mg, 94%).

Example 2

Preparation of a Stable Tetramethylrhodamine Based Labeling Reagent (Red Fluorescence) (M0774)

The stable labeling reagent N-(2-(1-(triisopropylsulfonylhydrazino)methylbenzene-4-yl)ethyl)-tetramethylrhodamine-5(&6)-carboxamide methyl ester (M0774) was prepared starting from commercially available 5(6)carboxytetramethylrhodamine (CTMR).

CTMR (50 mg, 120 μmol) was dissolved in dry DMF (1 mL) and treated with disuccinimidyl carbonate (66 mg, 260 μmole) and DMAP (10 mg), allowed to react for 18 hours at room temperature under anhydrous conditions until TLC analysis showed complete conversion to the succinimidyl ester. The reaction was quenched with water (50 μL, 30 min) and purified by preparative TLC (8:2 $CH_2Cl_2$:MeOH). Treatment of the reactive ester with 4-(2-aminoethyl)benzaldehyde hydrochloride (M0748: 28 mg, 150 umole, prepared as described in Example 1) and diisopropylethylamine (28 μL, 160 μmol) gave the stabilized N-(2-(1-Benzaldehyde-4-yl) ethyl)-tetramethylrhodamine-5(&6)-carboxamide form (M0762) which was purified by extraction with $CH_2Cl_2$ (20 mL) and washing with saturated sodium bicarbonate solution (2×20 mL); water (1×20 mL) and brine (1×20 mL). The resulting organic layer was dried over anhydrous sodium sulfate, filtered, evaporated and dried in vacuo. The resulting residue was purified by preparative TLC using 10% MeOH in $CH_2Cl_2$ to give a purple solid (M0762: 20 mg, 30%) homogeneous by TLC analysis. $^1$H-NMR (CDCl$_3$) δ: 10.0 (2s, 1H, CHO); 8.4 (s, 0.5H, aromatic); 8.2 (d, 0.5H, aromatic); 8.0 (q, 1H, aromatic); 7.8 (2d, 2H, aromatic); 7.3 (m, 3H); 6.5 (m, 6H, aromatic); 3.8 (q, 2H); 3.6 (q, 2H); 3.0 (s, 12H).

Conversion to the corresponding methyl ester was performed by treating M0762 with anhydrous HCl in MeOH (1N solution, 15 mL, 18 hours) followed by treatment with aqueous HCl (1 mL, 1N solution) to hydrolyze any acetal formed during ester formation to give the protected aldehyde (M0766: 13 mg, 60%)

The aldehyde M0766 (13 mg, 21 mmol) was converted to the corresponding 2,4,6-triisopropylphenylsulfonyl hydrazone by treatment with 2,4,6-triisopropylphenylsulfonyl hydrazide (7 mg, 23 μmole) in MeCN (750 μl) at room temperature for 15 hours. TLC analysis (8:2 $CH_2Cl_2$:MeOH) showed the reaction to be quantitative. The solvent was removed and the product crystallized from diethylether to give a dark purple solid (M0774: 19 mg, 100%). TLC: $SiO_2$ (irrigant=15% MeOH in $CH_2Cl_2$) $R_f$=0.43. $^1$H-NMR (CDCl$_3$) δ: 9.9 (s, 1H); 8.4 (s, 0.5H, aromatic); 8.2 (d, 0.5H, aromatic); 8.0 (q, 1H, aromatic); 7.9 (s, 1H); 7.8 (2d, 2H, aromatic); 7.3 (m, 3H); 7.1 (s, 2H, aromatic); 6.5 (m, 6H, aromatic); 3.9 (s, 3H); 3.8 (q, 2H); 3.7 (s, 1H); 3.6 (q, 2H); 3.5 (sep, 3); 3.0 (s, 12H); 1.2-1.4 (m, 18, alkyl).

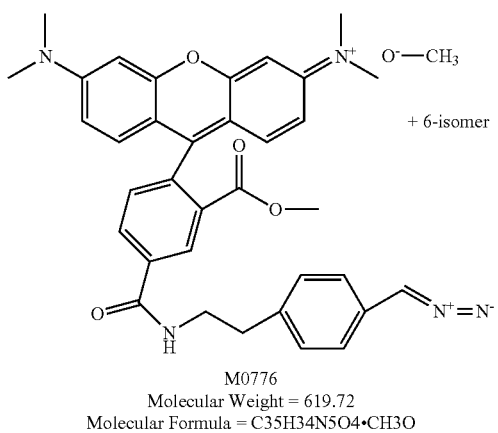

M0776
Molecular Weight = 619.72
Molecular Formula = C35H34N5O4•CH3O

Preparation of the reactive dye. Method 1. The reactive dye derivative, M0776 was prepared in situ by treating the aromaticsulfonylhydrazone (M0774, 1 mg, 1.1 μmole) with an excess of polymer-bound sodium 4-benzyloxybenzyl alkoxide (M1514, 5 mg, 5.5 umole) for 12 hours at room temperature in dimethylformamide. Treatment of the resulting M0776 with AcOH or ATP prior to the analysis gave quantitative reaction of the diazomethyl dye to a new $R_f$ product (8:2 $CH_2Cl_2$:MeOH) using silicagel TLC analysis.

Preparation of the reactive dye. Method 2. The reactive compound, M0776 could also be prepared by treating the aryl sulfonylhydrazone (M0774, 7 mg, 8 μmol) with an excess of NaOMe in MeOH (400 μL, 12.5% solution W/V) for 12 hours at room temperature. Water was added (3 mL) and the product extracted into $CH_2Cl_2$ (5×5 mL) with the combined organic layers being back-extracted with water (2×5 mL). The $CH_2Cl_2$ layers were filtered through a cotton plug, the solvent was removed and the product used directly for nucleotide labeling. An analytical sample of M0766 could be isolated by column chromatography on a silica gel column using 20% MeOH in dichloromethane as eluent.

Treatment of M0776 prepared by this method, with AcOH or ATP prior to the analysis gave quantitative reaction of the diazomethyl dye to a new $R_f$ using silica gel TLC analysis product (8:2 $CH_2Cl_2$:MeOH).

Example 3

Preparation of Rhodamine 110 Based Labeling Reagents. (Green Fluorescence) (M0847)

5(6)-Carboxyrhodamine 110 (2.05 grams, 4.99 mmol, mixed-isomers) and diisopropylethylamine (3.51 mL, 20.2 mmol) were dissolved in dry DMF (10 mL), cooled to –10° C. (methanol, ice bath) and trityl chloride (2.81 grams, 10.1 mmol) added slowly with stirring. The reaction mixture was allowed to warm to room temperature, and continued stirring overnight at ambient temperature under dry $N_{2(g)}$. The reaction mixture was then poured into ice-water (110 mL), and the pH of the solution adjusted to pH 3 using dilute aqueous HCl solution. This mixture was extracted with ethyl acetate until no more red product was found in the aqueous layer, by TLC analysis (3:3:0.3:0.1 MeOH:$CH_2Cl_2$:water:$NH_4OH$). The combined EtOAc layers were washed with water and brine (1×100 mL each), filtered and the organic layer evaporated to a red solid which was purified by silicagel 60 column chromatography (1×40 cm) using 20% methanol in dichloromethane as eluent. Fractions containing the pure product were combined, evaporated and dried in vacuo to give the ditrityl derivative M0694: 1.06 grams (25%).

A sample of M0694 (280 mg, 325 μmol) was suspended in warm DMF (12 mL), cooled to room temperature and disuccinimidyl carbonate (92 mg, 358 μmol) and N,N-dimethylaminopyridine catalyst (8 mg) added. After 20 min. the reaction was complete (TLC analysis; silicagel plate; EtOAc irrigant) and the mixture was diluted with ethylacetate (100 mL) and washed with ice-water and brine (2×50 mL each). The final organic layer was dried over anhydrous sodium sulfate, filtered and evaporated. Further drying in vacuo gave the succinimidyl ester as a red solid (M0696: 292 mg, 92%).

The succinimidyl ester M0696 (292 mg, 305 μmol) was dissolved in dry DMF (2 mL) and M0748 (85 mg, 458 μmol) and diisopropylethylamine (80 μL, 456 μmol) added. This mixture was allowed to stir at room temperature under dry $N_{2(g)}$ overnight until TLC (2:1 EtOAc:Hexanes) indicated approximately 80% conversion to the phenethylamide. The reaction mixture was diluted with ethylacetate (50 mL) and washed with water, dilute aqueous HCl solution, and dilute NaCl solution (2×50 mL each). The final organic layer was dried over anhydrous sodium sulfate, filtered, evaporated and purified by preparative TLC using 2 (20×20 cm) silicagel plates, 1 mm thickness) with development using 3:1 ethylacetate:hexanes as solvent. The individual product isomers could be isolated by elution from the $SiO_2$ plates using 10% MeOH/$CH_2Cl_2$ to give 61 mg and 62 mg respectively of the higher $R_f$ and lower $R_f$ isomers of M0811 (40% overall yield).

The individual (5- or 6-) isomers (M0811: 61, 62 mg each, 62 mmol each) were dissolved separately in 10% aqueous HCl in acetone and allowed to react for 20 min. until TLC showed conversion to a new product (1:1 MeOH:EtOAc irrigant). The solvent were removed by evaporation, dried in vacuo and treated with anhydrous 10% HCl in MeOH (5 mL) to convert M0811 to the methyl ester M0813. TLC analysis (1:1 EtOAc:MeOH) indicated the reaction was complete ($R_f$=0.82) after 4 days, the solvent was removed by evaporation, and the products purified by preparative TLC using 30% methanol in ethylacetate for elution. The yields of the deblocked aldehydes were 7 mg of each isomer M0813: 21%). $^1$H-NMR analysis (d$^6$-DMSO) indicated that the products existed as a mixture of free aldehyde (δ: 10.0 ppm) and Schiff's base (δ: 5.4 ppm) under neutral conditions.

The individual aldehyde isomers M0813 (7 mg, 12 μmol each) were converted to the corresponding 2,4,6-triisopropylphenylsulfonyl hydrazones (M1492) by treatment with 2,4, 6-triisopropylphenylsulfonyl hydrazide (4 mg, 14 umole) in MeOH (750 μL) and heating at reflux for 10 minutes followed by stirring at room temperature for 2 hours. TLC analysis (2:1 EtOAc:MeOH) showed the reactions to be virtually quantitative. The solvent was removed and the product crystallized from diethylether to give dark red solids.

The reactive dye compounds, M0847 (1 mg samples) were prepared in situ as described in Example 2 above using the polymer-based catalyst (Method 1) (M1514, 5 mg, 5.5 μmol) for 12 hours at room temperature in dry dimethylformamide.

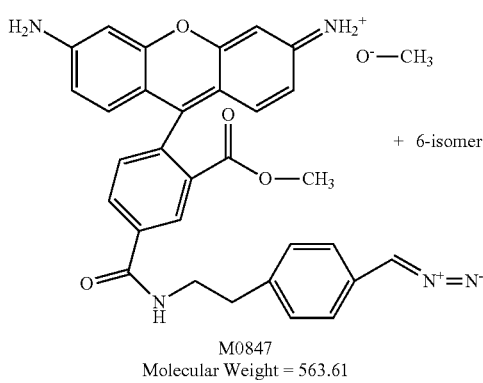

M0847
Molecular Weight = 563.61
Molecular Formula = C31H26N5O4•CH3O

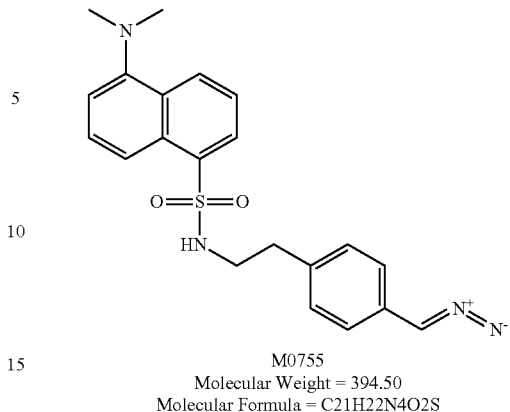

M0755
Molecular Weight = 394.50
Molecular Formula = C21H22N4O2S

Example 4

Preparation of a dimethylaminonaphthalenesulfonate, DANSYL Based Labeling Reagent. (Blue Fluorescence) (M0755)

Dansyl chloride (151 mg, 560 µmol) and 4-(2-aminoethyl) benzaldehyde hydrochloride (M0748: 99 mg, 533 µmol) were dissolved in dry DMF (3 mL) and diisopropylethylamine (195 µL, 1.12 mmol) added. This mixture was allowed to stir under anhydrous $N_2$(gas) at room temperature for 2 hours until TLC analysis showed complete conversion to a new product (1:1 EtOAc:hexanes, $R_f$=0.5). Ethylacetate (60 mL) was added and the solution washed with water, 10% HCl/water, water and brine (1×20 mL each). The organic layer was filtered through a cotton plug, the solvent removed by rotary evaporation reduced pressure, and the product purified by preparative TLC using 4:3 hexanes:ethylacetate as eluent. The band containing the pure product was removed from the plate and eluted with ethylacetate to give a yellow glass (M0749: 41 mg, 20%). $^1$H-NMR (CDCl$_3$) δ: 9.9 (s, 1H, CHO); 8.6 (d, 1H, aromatic); 8.2 (d, 1H, aromatic); 8.1 (d, 1H, aromatic); 7.6 (d, 2H, aromatic); 7.5 (t, 1H, aromatic); 7.4 (t, 1H, aromatic); 7.3 (s, 1H); 7.2 (d, 1H); 7.0 (d, 1H, aromatic); 4.6 (t, 1H); 3.2 (t, 2H); 2.9 (s, 6H, 2×—CH$_3$); 2.8 (t, 2H).

The aldehyde M0749 (11 mg, 290 mmol) was dissolved in acetonitrile (500 uL) and treated with triisopropylphenylsulfonyl hydrazide (7 mg, 37 µmol) with stirring for 1.5 hour at room temperature. The solvent was removed and the product triturated with diethylether to give the product as a yellow powder in quantitative yield (M0771: 19 mg, 100%).

This hydrazone was used to produce the final reactive labeling reagent (M0775: 11 mg/220 µl, 50 µg/µL) using the polymer-based method as in Example 2 (Method 1). Treatment of M0755 with acetic acid or CBZ-glycine gave complete conversion to new products by TLC analysis (1:1 EtOAc:hexanes).

Example 5

Preparation of a Long-Chain NBD-Based Labeling Reagent. (Blue-Green Fluorescence Emission) (M0773)

NBD-aminohexanoic acid, NHS ester (NBD-X-NHS 60 mg, 153 µmol) (prepared by treatment of NBD-Cl with aminohexanoic acid, and followed by synthesis of the NHS ester using NHS and EDC) was dissolved in dry DMF (1 mL) and M0748 (29 mg, 153 µmol) added followed by diisopropylethylamine (27 µl, 153 µmol). This reaction mixture was allowed to stir at room temperature overnight, diluted with EtOAc (7 mL) and washed with water (3×2 mL) and brine (1×2 mL). The EtOAc layer was dried over anhydrous sodium sulfate and filtered. The crude product was purified by preparative TLC using 3% methanol in dichloromethane for development. The product was eluted from the plate using ethylacetate as irrigant, filtered, and dried in vacuo to give a bright yellow product (M0759: 37 mg, 51%).

A sample of M0759 (9 mg, 21 µmol) was dissolved in dry acetonitrile (0.5 mL) and triisopropylphenylsulfonyl hydrazide (7 mg, 23 µmol) added. The reaction mixture was heated briefly to reflux to dissolve all reactants, and then allowed to stir at room temperature overnight. TLC analysis (2:1 CH$_2$Cl$_2$:EtOAc) showed complete conversion to the hydrazone M0772. The solvent was removed by evaporation and the product dried in vacuo overnight. This sample (15 mg) was used without further purification for production of the diazomethyl reactive labeling reagent using the polymer-based method with M1514 as described in Example 2.

A sample of the crude M0772 (5 mg, 7 µmol) was dissolved in methanol (200 µL) and 25% sodium methoxide in methanol (200 µL) added. After stirring at room temperature for 3 hours, the reaction was diluted with water, and extracted with dichloromethane (4×5 mL). The combined CH$_2$Cl$_2$ layers were back-extracted with brine solution (2×5 mL), filtered through a cotton plug, and the solvent removed by evaporation under reduced pressure. After drying in vacuo an orange solid (M0773: 2 mg, 70%) was obtained, which was dissolved in dry DMF (40 µL) to prepare a 50 µg/µL labeling solution for use in DNA/RNA analyses.

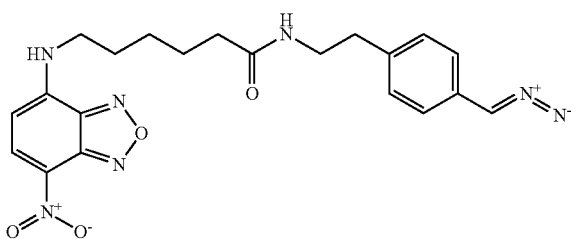

M0773
Molecular Weight = 437.46
Molecular Formula = C21H23N7O4

Example 6

Preparation of a Polymer-Bound Activation Reagent (M1514)

A sample of 4-Benzyloxybenzylalcohol, polymer-bound (Wang Resin, Aldrich Chemical Co. Product 520608 or the like, CAS [201058-08-4]) (1.54 grams, 1.54-2.32 mmole of alcohol) was suspended under anhydrous conditions in absolute, anhydrous methanol (20 mL) and 25% (w/v) sodium methoxide in methanol solution (0.264 mL, 4.64 mmole) added. This mixture was allowed to stir under a dry $N_{2(g)}$ atmosphere in anhydrous conditions for 2.5 hours, diluted with anhydrous methanol (10 mL) and centrifuged (1000 g, 5 min.). The supernatant solution was decanted, and the resin washed four times with additional anhydrous methanol (20 mL each) as above, with centrifugation and removal of the supernatant. The final resin was dried in vacuo overnight at room temperature to give a bright orange resin polymer 1.22 grams (80%).

Example 7

Preparation of Fluorescein-Based Labeling Reagents (M0755 and M0852) (Green Fluorescence)

Method A: (p-diazomethyl)phenethyl-5-thiouredyl fluorescein, methyl ester was prepared using a fluorescein isothiocyanate intermediate reaction with 4-(2-aminoethyl) benzaldehyde, followed by formation of the hydrazone using 2,4,6-triisopropylbenzenesulfonylhydrazide and polymer-based conversion to the diazomethyl reactive label. Briefly, 5-aminofluorescein (500 mg, 1.44 mmol) was added to a solution of anhydrous HCl/MeOH (10 mL, 1N) and allowed to stir at reflux for 18 hours until TLC analysis (1% MeOH/ EtOAc) indicated complete conversion to the methyl ester (M0744). The product was isolated by evaporation of the solvent, and purification on a column of silicagel 60 (2×25 cm) using gradient elution (2% (1 L), 5% (1 L) 20% (1 L) and 25% (0.5 L) MeOH in EtOAc. Fractions containing the purest fractions were rechromatographed on a second silicagel column (2×45 cm) with elution using 10% MeOH in $CH_2Cl_2$. Fractions containing the pure methyl ester were combined and evaporated and dried in vacuo to give a bright orange solid (M0744: 350 mg, 61%).

A sample of M0744 (50 mg, 126 μmol) was dissolved in dry DMF (6 mL) and diisopropylethylamine (75 μL, 430 μmol) followed by thiophosgene (12 μL, 150 μmol) added. This reaction mixture was allowed to stir under anhydrous conditions for 1 hour at room temperature, and 4-(2-aminoethyl)benzaldehyde hydrochloride (M0748: 19 mg, 100 μmol) and additional diisopropylethylamine (17 uL, 100 μmol) added. After stirring for 3 days, at room temperature the reaction mixture was treated with water (20 mL) and 10% aqueous HCl solution (3 mL), and extracted with ethylacetate (3×20 mL). The combined organic layers were back-extracted with water, 10% HCl/H2O, and brine solution (1×20 mL each), dried over anhydrous sodium sulfate, filtered and evaporated to an orange solid that was redissolved in MeOH and purified by preparative TLC (7.5% MeOH in $CH_2Cl_2$). The product band, containing the pure sample was eluted with 3:1 $CH_2Cl_2$:MeOH, filtered and evaporated to give M0752: 13 mg, 24%).

A solution of M0752 (2 mg) was treated with triisopropylbenzenesulfonylhydrazide (1.4 mg) in dry methanol (1 mL) and allowed to stir overnight at room temperature until TLC analysis (9:1 $CH_2Cl_2$:MeOH) indicated complete conversion to the hydrazone (M0781). M0781 was converted to the active diazo derivative in situ as described in Example 2 above using the polymer-based catalyst (M1514, 5 mg, 5.5 μmol) for 12 hours at room temperature in dimethylformamide to give the reactive dye derivative (M0755) in quantitative yield (2 mg). Samples of M0755 were prepared as DMF solutions that could be used directly for labeling studies as described below.

Method B: 5(6)-Carboxyfluorescein di-acetate, NHS ester (100 mg, 179 μmol) was suspended in dry DMF (2 mL) and M0748 (50 mg, 269 μmol) added followed by diisopropylethylamine (47 μL, 269 μmol). This reaction mixture was allowed to stir at room temperature under anhydrous conditions for 2 hours, diluted with ethylacetate (20 mL) and washed with saturated ammonium chloride solution, water and brine (1×20 mL each). The organic layer was dried over anhydrous sodium sulfate, filtered and dried in vacuo. Due to some partial deacetylation, the product was reacetylated using acetic anhydride and dry pyridine (1 mL each) at room temperature overnight. Workup as above gave the crude product as a single product by TLC (3:1 $CH_2Cl_2$:EtOAc). The crude product was purified using a preparative TLC plate (20×20 cm, 1 mm thickness) using 25% ethylacetate:dichloromethane eluent to give the aldehyde derivative M0848 as a colorless solid (62 mg, 58%).

The sample of M0848 (62 mg, 104 μmol) in methanol (3 mL) was treated with 2,4,6-triisopropylphenylsulfonyl hydrazide (34 mg, 115 μmol) and allowed to stir at room temperature for 3 hours until the reaction was shown to be complete by TLC. The sample was treated with concentrated $NH_4OH$ (2 drops) to pH 10 for 15 hours, then neutralized with dilute aqueous HCl (to pH 2) and extracted with ethylacetate (3×10 mL). The combined EtOAc layers were washed with water and brine (1×10 mL each) and then dried over anhydrous sodium sulfate, filtered and dried in vacuo to give a yellow solid (M0849: 90 mg, 100%).

M0849 (6 mg, 8 μmol) prepared in situ as described in Example 2 above using the polymer-based catalyst (M1514, 30 mg, 33 μmol) for 12 hours at room temperature in dimethylformamide to give the final product (M0852: 4 mg).

Example 8

Preparation of a Long-Wavelength Non-Symmetrical Di-Carbocyanine-Based Reactive Labeling Reagent (M0753)

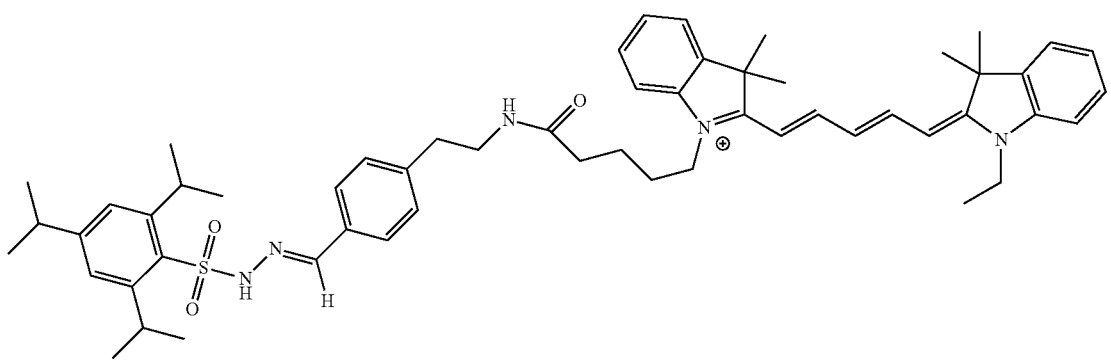 [SMILES: CCN1/C(=C/C=C/C=C/C2=[N+](CCCCC(=O)NCCc3ccc(/C=N/NS(=O)(=O)c4c(C(C)C)cc(C(C)C)cc4C(C)C)cc3)c3ccccc3C2(C)C)C(C)(C)c2ccccc21]

Monofunctional CY5-NHS ester (prepared according to the method of Ernst L, Gupta R K, Mujumdar R B, Waggoner A S, (1989) Cytometry 10: 3-10.; Jelinek C F, Kleinschmidt R F (1951) U.S. Pat. No. 2,549,097) (22 mg, 28 umole) and M0748 (5.6 mg, 30 μmol) in dry DMF (2 mL) is added diisopropylethylamine (5.3 μL, 30 μmol) and this reaction mixture allowed to stir at room temperature under dry $N_{2(g)}$ overnight. The DMF is evaporated under high vacuum (in vacuo) to give a dark blue solid that is resuspended in methanol (1.5 mL), filtered, and applied to a preparative TLC plate (10×20 cm) and eluted with 25% MeOH:$CH_2Cl_2$. The product is isolated by washing the silicagel with 1:1 methanol:dichloromethane, evaporated, dried and triturated with water, acetone, and diethylether to give the aldehyde as a dark blue solid, homogeneous by TLC analysis (irrigant=1:3 MeOH:$CH_2Cl_2$).

The aldehyde adduct (18 mg, 22 μmol) is dissolved in acetonitrile (2 mL) and treated with triisopropylphenylsulfonyl hydrazide (M1516) (7 mg, 22 μmol) with stirring for 1.5 hour at room temperature. The solvent is removed and the product triturated with diethylether to give the hydrazide product (M0753) as a blue glass in quantitative yield. This hydrazide is treated with 25% NaOMe/MeOH (w/v) (200 μL) in methanol (500 μL) (24 h) to convert it to the diazomethyl derivative. The reaction is diluted with water (2 mL) and extracted with $CH_2Cl_2$ (3×2 mL). The combined organic layers are filtered through a cotton plug, evaporated to dryness and redissolved in DMF (220 μL) to produce the CY5-C6-amidoethylphenyl-p-diazomethane reactive labeling reagent Treatment of this derivative with acetic acid or CBZ-glycine gives complete conversion to new products by TLC analysis (1:1 $CH_2Cl_2$:MeOH).

Example 9

Preparation of a Reactive Digoxigenin-Containing Labeling Compound (M0754)

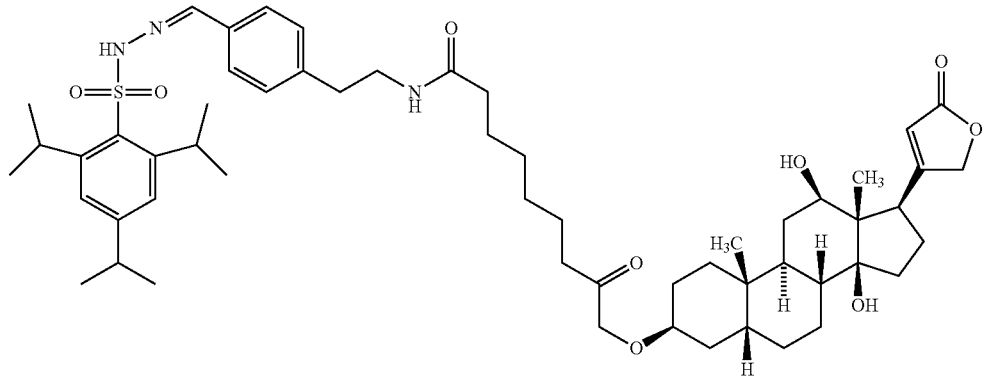

∈-(Digoxigenin-3-0-acetamido)caproic acid N-hydroxysuccinimide ester (Sigma-Aldrich, Prod. No. 55865) (18.5 mg, 28 umole) and M0748 (5.6 mg, 30 μmol) in dry DMF (2 mL) are added to diisopropylethylamine (5.3 μL, 30 μmol) and this reaction mixture allowed to stir at room temperature under dry $N_2$(gas) overnight. The DMF is evaporated under high vacuum (in vacuo) to give a colorless solid that is resuspended in dichloromethane (1.5 mL), filtered, and applied to a preparative TLC plate (20×20 cm) and eluted with 10%

MeOH:CH$_2$Cl$_2$. The product is isolated by washing the silicagel band containing the product with 1:1 methanol:dichloromethane, evaporation, drying and trituration with water, acetone, and diethylether to give the aldehyde as a colorless solid, homogeneous by TLC analysis (irrigant=1:3 MeOH:CH$_2$Cl$_2$).

The aldehyde adduct (21 mg, 22 μmol) is dissolved in acetonitrile (2 mL) and treated with triisopropylphenylsulfonyl hydrazide (4.2 mg, 22 μmol) with stirring for 15 hour at room temperature. The solvent is removed and the product triturated with diethylether to give the product (M0754) as a clear glass in quantitative yield. This hydrazide when treated with 25% NaOMe/MeOH (w/v) (200 μL) in anhydrous methanol:dichloromethane (500 μL) gives complete conversion to the diazomethyl derivative after 18 hours. The reaction is diluted with water (2 mL) and extracted with CH$_2$Cl$_2$ (3×2 mL). The combined organic layers are filtered through a cotton plug, evaporated to dryness and redissolved in DMF (100 μL) to produce the final digoxigenin-C6-amidoethylphenyl-p-diazomethane reactive labeling reagent. Treatment of this derivative with acetic acid or CBZ-glycine gives complete conversion to new products by TLC analysis (1:1 CH$_2$Cl$_2$:MeOH).

Example 10

Preparation of an Alternate Aldehyde Containing Linking Arm for Labeling Reagents. (M0686)

A sample of N-t-boc-amido-dPEG™$_4$ Acid (Quanta-BioDesign) (119 mg, 325 μmol) is suspended in warm DMF (12 mL), cooled to room temperature and disuccinimidyl carbonate (92 mg, 358 μmol) and N,N-dimethylaminopyridine catalyst (21 mg) added. After 60 min. the reaction is complete (TLC analysis; silicagel plate; EtOAc irrigant) and the mixture was diluted with ethylacetate (100 mL) and washed with ice-water and brine (2×50 mL each). The final organic layer is dried over anhydrous sodium sulfate, filtered and evaporated. Further drying in vacuo gave the succinimidyl ester (M0680), homogeneous by TLC analysis.

The succinimidyl ester M0680 (141 mg, 305 μmol) is dissolved in dry DMF (2 mL) and M0748 (85 mg, 458 μmol) and diisopropylethylamine (80 μL, 456 μmol) added. This mixture is allowed to stir at room temperature under dry N$_2$(g) overnight until TLC (2:1 EtOAc:Hexanes) indicates conversion to the phenethylamide. The reaction mixture is diluted with ethylacetate (50 mL) and washed with water, dilute aqueous HCl solution, and dilute NaCl solution (2×50 mL each) with the final organic layer dried over anhydrous sodium sulfate, filtered, evaporated and purified by preparative TLC using 2 20×20 cm silicagel plates, 1 mm thickness) with development using 75% ethylacetate:25% hexanes. The product is isolated by elution from the SiO$_2$ using 40% MeOH/CH2Cl2 to give 103 mg of M0683 (68% overall yield).

M0683 (103 mg, 0.21 mmol) is dissolved in 10% aqueous HCl in acetone and allowed to react for 20 min. until TLC showed conversion to a new product (1:1 MeOH:EtOAc irrigant). The solvents are removed by evaporation and the products purified by preparative TLC using 30% methanol in ethylacetate for elution. The yields of the deblocked aldehyde is 80 mg of M0686: 96%).

Example 11

Preparation of a Reactive Pyrene-Containing Labeling Reagent Using Direct Attachment of the Reactive Diazo Function to the Detection Agent. (M0668)

Pyrenecarboxyaldehyde (250 mg, 1.08 mmol) was dissolved in absolute ethanol (20 mL), cooled to 0° C. (ice-bath) and hydrazine hydrate (658 μL, 13.56 mmol) added slowly with stirring. This mixture was allowed to stir at 0° C. for 3 hours, warmed to room temperature and evaporated to dryness under reduced pressure (rotovap), reevaporated with absolute ethanol (3×15 mL) and dried in vacuo overnight to give the hydrazone (M0649) as a yellow solid (216 mg, 86%) homogeneous by TLC analysis. The hydrazone (M0649: 172 mg, 0.704 mmol) was dissolved in dry DMF (3 mL) and manganese dioxide (solid, 392 mg, 4.50 mmol) added. This suspension was allowed to stir at room temperature for 1 hour, filtered and the resulting DMF solution of the title compound (M0668) (approximately 50 mg/mL) used directly for labeling nucleotides (5 mg samples, AMP and GMP). Briefly, samples of the nucleotides were dissolved in water (1 mL) and 500 uL of the diazomethylpyrene labeling compound (M0668) (50 mg·mL) added to each sample. After brief sonication, the samples were placed in an incubator at 37° C. for one hour, and subjected to HPLC analysis using a Prosphere 300A C18 column (Alltech Assoc., 5 u, 250×4.6 mm) using gradient elution and solvent A: 50 mM ammonium phosphate buffer (pH 4.5); solvent B: 3.25% acetonitrile:water, 1 mL/min. (linear gradient, 20 min.). This HPLC analysis exhibited virtually quantitative conversion to the pyrene labeled phosphodiesters (M0656 for AMP and M0678 for GMP) and no reaction with the parent bases adenosine or guanosine using the same method.

Example 12

Preparation of a Reactive Fluorescein-Containing Labeling Compound with an Alternate Linking Arm 3-(4-formylphenyl)propanoic acid (230 mg, 1.29 mmol) is suspended in warm DMF (12 mL), cooled to room temperature and disuccinimidyl carbonate (333 mg, 1.30 mmol) and N,N-dimethylaminopyridine catalyst (22 mg) added. After 3 hours the reaction is complete (TLC analysis; silicagel plate; EtOAc irrigant) and the mixture was diluted with ethylacetate

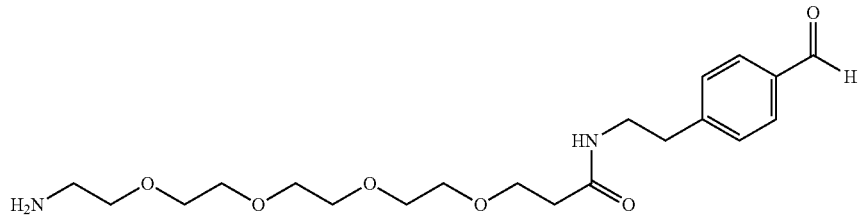 [SMILES: NCCOCCOCCOCCOCCC(=O)NCCc1ccc(C=O)cc1]

(100 mL) and washed with ice-water and brine (2×50 mL each). The final organic layer is dried over anhydrous sodium sulfate, filtered and evaporated. Further drying in vacuo gave the 3-(4-formylphenyl)propanoic acid, succinimidyl ester M0723, homogeneous by TLC analysis.

Fluoresceinamine, Isomer I (5-aminofluorescein, 382 mg, 1.10 mmol) is dissolved in dry DMF (3 mL) and 3-(4-formylphenyl)propanoic acid, succinimidyl ester (M0723: 305 mg, 1.11 mmol) is added with stirring followed by diisopropylethylamine (200 µL, 1.15 mmol) and this reaction mixture is allowed to stir at room temperature for 12 hours under anhydrous conditions until TLC analysis shows complete conversion to the amide, which is purified by extraction with $CH_2Cl_2$ (20 mL) and saturated sodium bicarbonate solution (2×20 mL); water (1×20 mL) and brine (1×20 mL). The organic layer is dried over anhydrous sodium sulfate, filtered, evaporated and dried in vacuo. The resulting residue is purified by preparative TLC using 10% MeOH in $CH_2Cl_2$ to give fluorescein 5-amidopropylphenyl-4-carboxaldehyde (M0775) as an orange solid.

The sample of M0775 (444 mg, 0.88 mol) in methanol (3 mL) is treated with anhydrous 10% HCl in MeOH (25 mL) to convert M0775 to the methyl ester M1571. TLC analysis (1:1 EtOAc:MeOH) indicated the reaction was complete ($R_f$=0.82) after 4 days, the solvent was removed by evaporation, and the products purified by preparative TLC using 30% methanol in ethylacetate for elution.

The sample of M1571 (457 mg, 0.88 mol) in methanol (30 mL) is treated with 2,4,6-triisopropylphenylsulfonyl hydrazide (290 mg, 0.97 mmol) and allowed to stir at room temperature for 3 hours until the reaction is shown to be complete by TLC. The sample is treated with conc. $NH_4OH$ to pH 10 for 15 hours, then neutralized with dilute aqueous HCl (to pH 2) and extracted with ethylacetate (3×10 mL). The combined EtOAc layers are washed with water and brine (1×10 mL each) and then dried over anhydrous sodium sulfate, filtered and dried in vacuo to give the hydrazide (M1572) as an orange solid (704 mg, 100%). A sample of the hydrazide (6 mg, 8 µmol) is dissolved in methanol (500 µL) and treated with NaOMe/MeOH (200 µL) and allowed to stir at room temperature overnight. After removing the solvents, the product is redissolved in ethylacetate (10 mL) and water (10 mL) extracted with water (2×10 mL). The ethylacetate layer is filtered through a cotton plug and evaporated to dryness and dried in vacuo to give the reactive labeling reagent 5-(3-amidopropyl-4'-diazomethylphenyl)fluorescein (M1573: 4 mg) as an orange glass.

Example 13

Preparation of a Reactive Tetramethyl Rhodamine-Containing Labeling Compound with an Alternate Linking Arm (M0693)

5(6)-carboxytetramethylrhodamine (CTMR: 50 mg, 120 µmol) is dissolved in dry DMF (1 mL) and treated with disuccinimidyl carbonate (66 mg, 260 µmol) and DMAP (10 mg) and allowed to react for 18 hours at room temperature under anhydrous conditions until TLC analysis shows complete conversion to the succinimidyl ester. The reaction is quenched with water (50 µL), 30 min and purified by preparative TLC (8:2 $CH_2Cl_2$:MeOH). Reaction of the reactive ester with amino-dPEG4 amidoethylbenzaldehyde (M0686: 28 mg, 150 µmol) and diisopropylethylamine 28 µL, 160 µmol) gave the key N-(2-(1-Benzaldehyde-4-yl)ethyl)-PEG4-tetramethylrhodamine-5-(&6)-carboxamide intermediate (M0689) which is purified by extraction with CH2Cl2 (20 mL) and saturated sodium bicarbonate solution (2×20 mL); water (1×20 mL) and brine (1×20 mL). The organic layer was dried over anhydrous sodium sulfate, filtered, evaporated and dried in vacuo. The resulting residue was purified by preparative TLC using 10% MeOH in $CH_2Cl_2$ to give a purple solid (M0689: 20 mg, 30%) homogeneous by TLC analysis.

Conversion to the corresponding methyl ester was performed by treating M0689 with anhydrous HCl in MeOH (15 mL, 1N solution, 18 hours) followed by treatment with aqueous HCl (1 mL, 1N solution) to hydrolyze any acetal formed during ester formation to give the protected intermediate (M0691: 13 mg, 60%)

The aldehyde M0691 (13 mg, 21 µmol) is converted to the corresponding 2,4,6-triisopropylphenylsulfonyl hydrazone by treatment with 2,4,6-triisopropylphenylsulfonyl hydrazide (7 mg, 23 µmol) in MeCN (750 µL) at room temperature for 15 hours where TLC analysis (8:2 $CH_2Cl_2$:MeOH) shows the reaction to be quantitative. The solvent is removed and the product crystallized from diethylether to give a dark purple solid (19 mg, 100%)

The title compound, TMR-methyl ester-5(6)carboxyamido-dPEG™4 amidoethyldiazomethylphenyl, M0693 is prepared as a mixture of isomers by treating the sulfonylhydrazone (7 mg, 8 µmol) with an excess of NaOMe in MeOH (400 µL, 12.5% solution W/V) for 12 hours at room temperature. Water is added (3 mL) and the product extracted with $CH_2Cl_2$ (5×5 mL) with the combined organic layers being back-extracted with water (2×5 mL). The $CH_2Cl_2$ layers are filtered through a cotton plug, the solvent is removed and the product isolated by column chromatography (silica gel, 20% MeOH in dichloromethane). Treatment of M0693 with AcOH or ATP prior to the analysis gives quantitative reaction of the diazomethyl dye to a new Rf product (8:2 $CH_2Cl_2$:MeOH) using silicagel TLC analysis.

Example 14

Preparation of a Biotin-Containing Labeling Reagent (M0789)

To a solution of biotinylamidocaproic acid-N-hydroxysuccinimide ester (biotin-X-NHS; 100 mg, 0.22 mmol) and M0748 (43 mg, 0.23 mmol) in dry DMF (4 mL) was added diisopropylethylamine (80 µL, 0.46 µmol) and this reaction mixture allowed to stir at room temperature under dry $N_2(g)$ overnight. EtOAc (25 mL) was added to precipitate the product. The solids were isolated by centrifugation and washed with EtOAc (3×10 ml) and 1:9 MeOH:EtOAc (1×10 ml). The solids were dried in vacuo to give a white solid. (M0784: 70 mg, 65%) homogeneous by TLC analysis (irrigant=15% MeOH in $CH_2Cl_2$).

A sample of M0784 (50 mg, 102 µmol) was dissolved in methanol (2 mL). Triisopropylsulfonyl hydrazide (32 mg, 107 µmol) was added and this reaction mixture allowed to stir at room temperature under dry $N_{2(g)}$ overnight. The solvent was removed in vacuo and the resulting solids were tritrated with diethyl ether (2×5 mL) followed by EtOAc (1×5 mL). The solids were purified on a column of silicagel 60 (2.5×11 cm) using a gradient elution (5% (200 mL), 10% (600 mL), 20% (200 mL), 50% (100 mL) MeOH in $CH_2Cl_2$). Fractions containing the pure fractions were concentrated in vacuo to give a white solid. (M0789: 38 mg, 48%) homogenous by TLC analysis (irrigant=15% MeOH in $CH_2Cl_2$). $^1$H-NMR (DMSO-$d^6$) δ: 11.7 (s, 1H, NH); 7.9 (s, 1H, CHN); 7.7-7.8 (m, 2H, NH); 7.4 (d, 2H, aromatic); 7.3 (s, 2H, aromatic); 7.2 (d, 2H, aromatic); 6.4 (s, 1H, NH); 6.3 (s, 1H, NH); 4.6 (quin, 1H, alkyl); 4.1-4.2 (m, 2, alkyl); 3.1-3.2 (m, 4H, alkyl); 2.6-3 (m, 8H, alkyl); 2 (m, 4H, alkyl); 1-1.6 (m, 31, alkyl).

The stable precursor M0789 (11 mg, 20 μmol, theoretical) was converted to the active diazo derivative M0787 prepared in situ as described in Example 2 above using the polymer-based catalyst (Method 1) (M1514, 100 mg, 110 μmol) for 12 hours at room temperature in dry dimethylformamide. The reaction mixture was filtered and the solvent evaporated in vacuo to give the activated labeling compound (M0787: 10 mg, 100%) as an off white solid. Solutions of the active diazo-labeling compound were stable in solution (dry DMF) for up to two weeks after synthesis, if stored desiccated at −20° C.

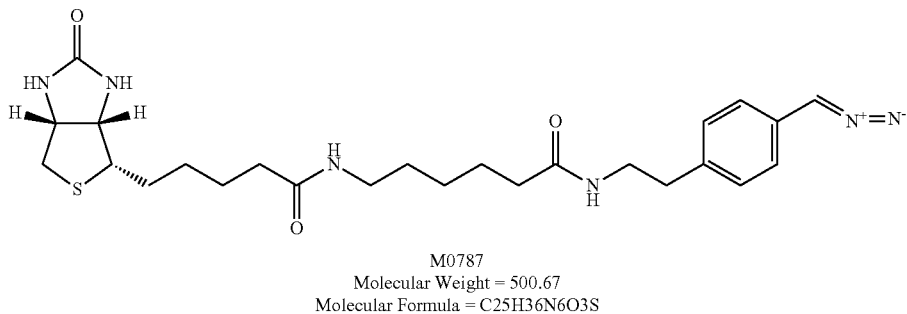 [SMILES: [N-]=[N+]=Cc1ccc(CCNC(=O)CCCCCNC(=O)CCCC[C@@H]2SC[C@@H]3NC(=O)N[C@@H]32)cc1]

M0787
Molecular Weight = 500.67
Molecular Formula = C25H36N6O3S

Example 15

Preparation of a Long-Chain NBD-Based Labeling Reagent with an Alternate Sulfonyl Hydrazone. (Blue-Green Fluorescence Emission) (M1484)

NBD-aminohexanoic acid, NHS ester (NBD-X-NHS 200 mg, 510 μmol) (prepared by treatment of NBD-Cl with aminohexanoic acid, and followed by synthesis of the NHS ester using NHS and EDC) was dissolved in dry DMF (3 mL) and M0748 (95 mg, 510 μmol) added followed by diisopropylethylamine (89 μl, 510 μmol). This reaction mixture was allowed to stir at room temperature overnight, diluted with EtOAc (20 mL) and washed with water (3×10 mL) and brine (1×10 mL). The EtOAc layer was dried over anhydrous sodium sulfate and filtered. The crude product was purified on a column of silicagel 60 (2.5×18 cm) using MeOH in $CH_2Cl_2$ (3%) as eluent. The pure fractions were concentrated and dried in vacuo to give a bright yellow product (M0759: 136 mg, 62%) homogeneous by TLC analysis (irrigant=3% MeOH in $CH_2Cl_2$).

A sample of M0759 (136 mg, 32 μmol) was dissolved in MeOH (5 mL) and p-toluenesulfonyl hydrazide (65.5 mg, 0.35 μmol) added. The reaction mixture was allowed to stir at room temperature overnight at room temperature. TLC analysis (9:1 $CH_2Cl_2$:MeOH) showed complete conversion to the hydrazone M1484. The precipitated solids were filtered and rinsed with MeOH (2×1 mL) and dried in vacuo overnight to give a bright yellow product (M1484: 165 mg, 87%) homogenous by TLC analysis (irrigant=10% MeOH in CH2Cl2). $^1$H-NMR (DMSO-$d^6$) δ: 11.3 (s, 1H, NH); 9.5 (s, 1H, NH); 8.2 (d, 1H, aromatic); 7.9 (s, 1H, aromatic); 7.8 (d, 1H, aromatic); 7.45 (d, 2H, aromatic); 7.35 (d, 2H, aromatic); 7.2 (d, 2H, aromatic); 6.4 (d, 1H, aromatic); 3.4 (m, 2H, alkyl); 3.2 (q, 2H, alkyl); 2.65 (t, 2H, alkyl); 2.25 (s, 3H, alkyl); 2 (t, 2H, alkyl); 1.6 (quint, 2H, alkyl); 1.5 (quint, 2H, alkyl); 1.3 (m, 2H, alkyl).

Example 16

Preparation of a Stable Tetramethylrhodamine Based Labeling Reagent (Red Fluorescence) with an Alternate Sulfonyl Hydrazone (M1483)

The stable labeling reagent N-(2-(1-(p-toluenesulfonylhydrazino)methylbenzene-4-yl)ethyl)-tetramethylrhodamine-5 (&6)-carboxamide methyl ester (M1483) was prepared starting from commercially available 5(6)carboxytetramethylrhodamine (CTMR). CTMR (216 mg, 500 μmol) was dissolved in dry DMF (1 mL) and treated with disuccinimidyl carbonate (154 mg, 600 μmol) and DMAP (31 mg) and allowed to react for 18 hours at room temperature under anhydrous conditions until TLC analysis showed complete conversion to the succinimidyl ester. The solvent was removed and the residue dissolved in $CH_2Cl_2$ (100 mL). The solution was extracted with saturated NaCl (2×100 mL), dried over $Na_2SO_4$ and the solvent removed to provide 380 mg crude reactive ester. Reaction of the reactive ester with 4-(2-aminoethyl)benzaldehyde hydrochloride (M0748: 94 mg, 500 μmol) and diisopropylethylamine (193 μL, 1.1 mmol) gave the key N-(2-(1-Benzaldehyde-4-yl)ethyl)-tetramethylrhodamine-5(&6)-carboxamide intermediate (M0762) which was purified by extraction with $CH_2Cl_2$ (100 mL) and saturated sodium bicarbonate solution (2×50 mL); water (1×50 mL) and brine (1×50 mL). The organic layer was dried over anhydrous sodium sulfate, filtered, evaporated and dried in vacuo. The crude product was purified on a column of silicagel 60 (2.5×23 cm) using a gradient elution (20:1:1 (450 mL), 20:2:1 (210 mL), 20:4:1 (630 mL), 20:8:1 (300 mL), 10:10:1 (200 mL) $CH_2Cl_2$:MeOH:AcOH). Fractions containing the pure product were concentrated in vacuo to give a red solid. (M0762: 60 mg, 30%) homogeneous by TLC analysis. $^1$H-NMR (CDCl$_3$) δ: 10.0 (2s, 1H, CHO); 8.4 (s, 0.5H, aromatic); 8.2 (d, 0.5H, aromatic); 8.0 (q, 1H, aromatic); 7.8 (2d, 2H, aromatic); 7.3 (m, 3H); 6.5 (m, 6H, aromatic); 3.8 (q, 2H); 3.6 (q, 2H); 3.0 (s, 12H).

Conversion to the corresponding methyl ester was performed by treating M0762 with anhydrous HCl in MeOH (15 mL, 1N solution, 18 hours) followed by treatment with aqueous HCl (1 mL, 1N solution) to hydrolyze any acetal formed during ester formation to give the unisolated intermediate (M0766)

The aldehyde M0766 (65 mg, 107 μmol) was converted to the corresponding p-toluenesulfonyl hydrazone by treatment with p-toluenesulfonyl hydrazide (21.9 mg, 118 μmole) in MeOH (5 mL) at room temperature for 15 hours. The solvent was removed and the solids were purified on a column of silicagel 60 (2.5×14 cm) using a gradient elution (0% (200 mL), 10% (500 mL), 20% (300 mL), 30% (200 mL) MeOH in $CH_2Cl_2$). (M1483:28 mg, 33%). TLC $SiO_2$ (irrigant=10% MeOH in $CH_2Cl_2$) $R_f$=0.24. $^1$H-NMR ($CDCl_3$) δ: 8.9 (t, 1H); 8.2 (2s, 1H, aromatic); 8.2 (d, 1H, aromatic); 7.9 (s, 2H, aromatic); 7.85 (d, 2H, aromatic); 7.4 (2d, 2H, aromatic); 7.3 (m, 4H); 7.1 (s, 21-1, aromatic); 6.5 (m, 4H, aromatic); 3.9 (s, 3H); 3.8 (dt, 2H); 3.7 (s, 1H); 3.4 (s, 3H); 2.9 (s, 12H); 2.8 (t, 2H).

Example 17

Preparation of Symmetrical Dicarbocyamine

Cy3-N,N'-bis-(N-[2-(4-triisopropylbenzenesulfonyl-hydrazone]-phenyl)-ethylcarbamoyl])-bis-propionamide (M1556)

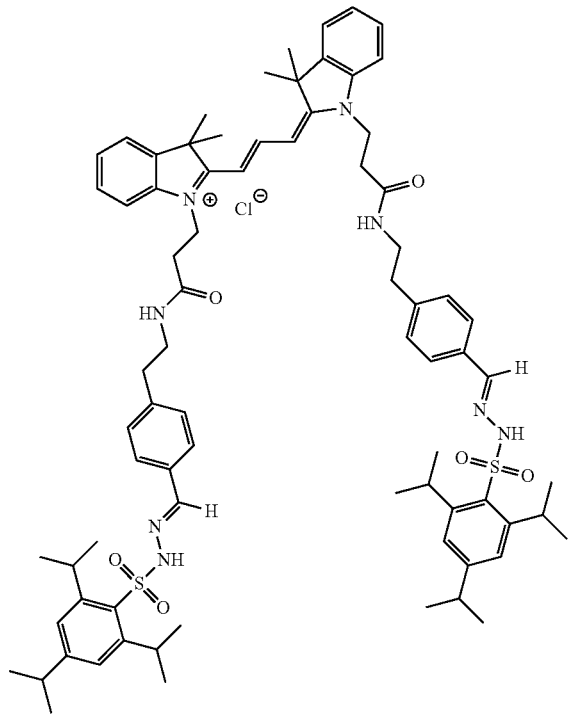 [SMILES: CC(C)c1cc(C(C)C)c(S(=O)(=O)N/N=C/c2ccc(CCNC(=O)CCN3/C(=C/C=C/C4=[N+](CCC(=O)NCCc5ccc(/C=N/NS(=O)(=O)c6c(C(C)C)cc(C(C)C)cc6C(C)C)cc5)c5ccccc5C4(C)C)C(C)(C)c4ccccc43)cc2)c(C(C)C)c1 ; [Cl-]]

A mixture of N-3-Carboxypropyl tri-methyl indolenine bromide (M1382) (0.99 g, 3.1 mmol, 1 equiv) and dry N,N-dimethylformamide was heated 16 hrs at 140° C. under anhydrous conditions to give the carbocyanine-N,N'-bis-propionic acid (M1525) (380 mg, 0.686 mmol). The reaction was diluted with $EtOAc:H_2O$ and the aqueous layer separated and extracted with dichloromethane (3×50 mL). The combined organic layers were washed with $H_2O$ and saturated NaCl solution (50 mL each), and dried over anhydrous $Na_2SO_4$. Purification of crude product by silicagel chromatography (80 mL) using a gradient elution system 700 mL of 5% MeOH in $CH_2Cl_2$, 325 mL of 10% MeOH in $CH_2Cl_2$, 650 mL of 12.5% MeOH in $CH_2Cl_2$, and 262.5 mL of 20% MeOH in $CH_2Cl_2$.

Under anhydrous conditions, a solution of the dicarbocyanine (0.40 g, 0.72 mmol, 1.0 equiv), N,N'-dicyclohexylcarbodiimide (0.313 g, 1.516 mmol, 2.1 equiv) and N,N'-diisopropylethylamine (5.2 equiv) in dry N,N-dimethylformamide (10 mL) was allowed to stir for 30 minutes at room temperature. 2-aminoethylbenzaldehyde hydrochloride (M0748) (0.282 g, 1.520 mmol, 2.1 equiv) was added and the reaction allowed to stir at ambient temperature for 24 hrs. After 24 hrs, 2 equivalents of the N,N'-diisopropylethylamine and N,N'-dicyclohexylcarbodiimide were added which was followed by 2 equivalent of the aldehyde, 30 minutes later. This reaction mixture was left to stir for an additional 4 hrs before completion of reaction was verified via TLC and formation of dicyclohexylurea precipitate. Finally addition of $H_2O$ (1.0 mL) converted the trace amounts of remaining dicyclohexylcarbodiimide to dicyclohexylurea. The reaction was vacuum filtered and the precipitate discarded while the filtrate was extracted 3×50 mL $CH_2Cl_2$ and $H_2O$. Followed by extraction with 50 mL of saturated $NaCl_{(aq)}$ and drying with $Na_2SO_4$ for 20 minutes. The final organic layer was filtered and reduced under low pressure to give the carbocyanine N,N'-bis-(N-[2-(4-formyl-phenyl)-ethylcarbamoyl])-bis-propionamide (M1550).

The carbocyanine-N,N'-bis-(N-[2-(4-formyl-phenyl)-ethylcarbamoyl])-bis-propionamide (M1550) (0.016 g, 0.02 mmol, 1.0 equiv) was dissolved in dry acetonitrile (3 mL) and triisopropylbenzenesulfonyl hydrazide (M1516) (0.013 g, 0.045 mmol, 2.2 equiv) added to under anhydrous conditions. This reaction mixture was allowed to stir at room temperature for 16 hours, after which time the solvent was removed under low pressure distillation (rotovap) and the residue co-evaporated 2× with acetonitrile (10 mL) to give the final hyrozine derivative, carbocyanine-N,N'-bis-(N-[2-(4-triisopropylbenzenesulfonylhydrazone]-phenyl)-ethylcarbamoyl])-bis-propionamide (M1556) (0.03 g, 0.02 mmol, 1.0 equiv, 109% yield) of sufficient purity for use in labeling reactions.

Example 18

Preparation of Symmetrical tricarbocyanine

N,N'-bis-(N-[2-(4-triisopropylbenzenesulfonyl-hydrazone]-phenyl)-ethylcarbamoyl])-bis-propionamide tricarbocyanine (M1557)

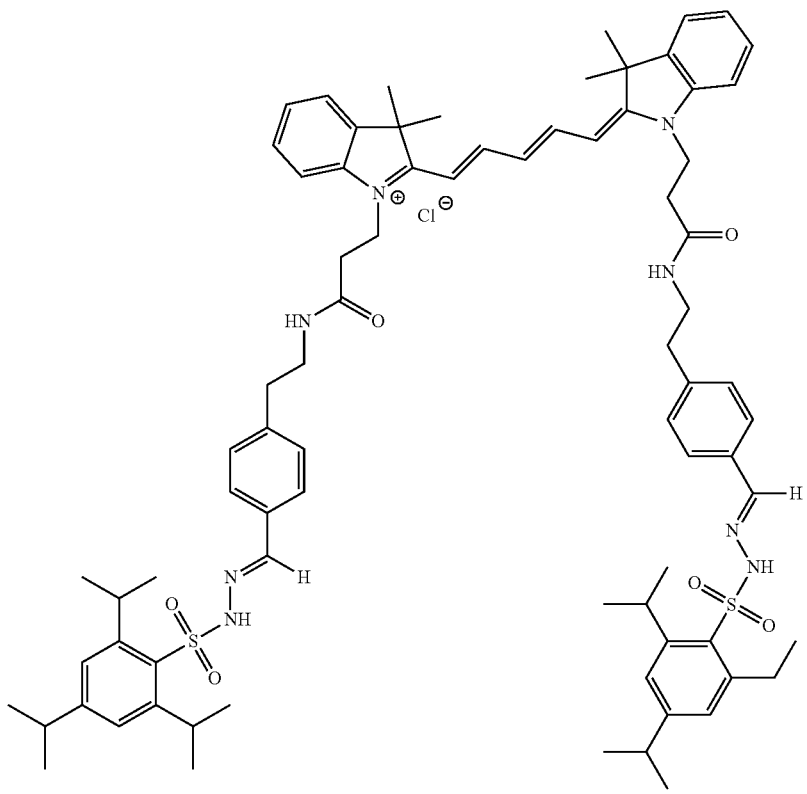 [SMILES: CCc1cc(C(C)C)cc(C(C)C)c1S(=O)(=O)N/N=C/c1ccc(CCNC(=O)CCN2/C(=C/C=C/C=C/C3=[N+](CCC(=O)NCCc4ccc(/C=N/NS(=O)(=O)c5c(C(C)C)cc(C(C)C)cc5C(C)C)cc4)c4ccccc4C3(C)C)C(C)(C)c3ccccc32)cc1 ; [Cl-]]

N-3-Carboxypropyl tri-methyl indolenine bromide (M1382) (1.00 g, 3.2 mmol, 1 equiv), trimethoxypropene (1.31 g, 9.61 mmol, 3 equiv) and dry pyridine (10 mL) were heated to 120° C. under anhydrous conditions to give dicarbocyanine N,N'-bis-propionic acid (M1548) (0.17 g, 0.32 mmol, 20% yield) after 5 hours. Work up included extracting the product into dichloromethane (3×50 mL) and washing the combined organic layer with $H_2O$ (50 mL) and saturated $NaCl_{(aq)}$ solution (1×50 mL) and drying with $Na_2SO_4$ for 20 minutes. Purification was carried out using silicagel 60 column chromatography (150 mL) using 1000 mL of 5% MeOH in $CH_2Cl_2$, 500 mL of 10% MeOH in $CH_2Cl_2$, and 500 mL of 12.5% MeOH in $CH_2Cl_2$ as eluents. Fractions containing the pure CY5 dye M1548 product were combined and evaporated to dryness.

Under $N_{2(g)}$, the Cy5 (0.17 g, 0.31 mmol, 1.0 equiv) product (M1548) was added to N,N'-dicyclohexylcarbodiimide (0.138 g, 0.668 mmol, 2.1 equiv) using N,N'-diisopropylethylamine (5.2 equiv) as the base in dry N,N-dimethylformamide (10 mL). After 30 minutes, 2-aminoethylbenzaldehyde hydrochloride (M0748) (0.123 g, 0.662 mmol, 2.1 equiv) was added to the reaction flask and left to stir at 24° C. for 24 hrs. After 24 hrs, 2 equivalents of the N,N'-diisopropylethylamine and N,N-dicyclohexylcarbodiimide were added which was followed by 2 equivalents of the aldehyde 30 minutes later. The reaction was left to stir for an additional 4 hrs before completion of reaction was verified via TLC and formation of precipitant. Work up included addition of $H_2O$ to convert the trace amounts of dicyclohexylcarbodiimide to dicyclohexylurea. The reaction was vacuum filtered and the precipitate discarded while the filtrate was extracted into $CH_2Cl_2$ (3×50 mL) and washed with $H_2O$ (50 mL) followed by extraction with saturated $NaCl_{(aq)}$ solution (50 mL) and drying with $Na_2SO_4$ for 20 minutes. $^1$H-NMR ($CDCl_3$) δ: 9.9 (d, 2H); 7.7 (m); 7.4-7.2 (m); 4.3 (t, 2H).

The product was reduced under high pressure to give dicarbocyamine N,N'-bis-(N-[2-(4-formyl-phenyl)-ethylcarbamoyl])-bis-propionamide (M1554) (0.250 g, 0.313 mmol, 1.0 equiv) which was reacted with triisopropylbenzenesulfonyl hydrazide (M1516) (0.206 g, 0.690 mmol, 2.2 equiv) and acetonitrile (10 mL) to give the final protected hydrazide derivative, dicarbocyamine N,N'-bis-(N-[2-(4-triisopropyl-benzenesulfonylhydrazone]-phenyl)-ethylcarbamoyl])-bis-propionamide (M1557) (0.426 g, 0.313 mmol, 1 equiv). The product could be further purified by co-evaporation with acetonitrile (2×30 mL) and concentrating under high pressure.

Example 19

Preparation of a Neutral Green 7H-Benz[de]benzimidazo[2,1-a]isoquinoline-7-one Dye Labeling Reagent. Synthesis of 3-[2-(4-triisopropylsulfonylhydrazide)phenyl)ethylaminocarbonyl]-7H-benz[de]benzimidazo[2,1-a]isoquinoline-7-one (M1797)

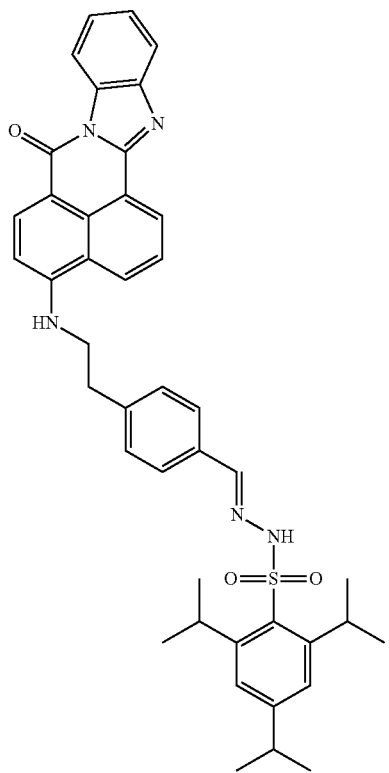 [SMILES: CC(C)c1cc(C(C)C)c(S(=O)(=O)N/N=C/c2ccc(CCNc3ccc4c(=O)n5c6ccccc6nc5c5cccc3c45)cc2)c(C(C)C)c1]

In a dry 100 mL round bottom flask 4-bromo-1,8-naphthalenedicarboxylic anhydride (5.0 g, 18 mmol) and o-phenylenediamine (2.4 g, 22 mmol), were dissolved in glacial acetic acid (50 mL) and the mixture refluxed for 3 hours. After this time, the reaction mixture was cooled to room temperature, and the products were extracted into dichloromethane and washed with water (2×100 mL). The organic layer was dried over anhydrous MgSO4, filtered and evaporated to dryness. The Rf value of 3'-bromo isomer by TLC (SiO2, irrigant=toluene) was slightly higher (Rf=0.36) than that of the 3-isomer (Rf=0.34). Therefore, the 3- and 3'-isomers were separated by column chromatography (SiO2, toluene), and the final single 3-bromo isomer recrystallized from toluene.

To a solution of 3-bromo-7H-benz[de]benzimidazo[2,1-a]isoquinoline-7-one (350 mg, 1 mmol) in 2-methoxyethanol (10 ml) copper(II) sulfate pentahydrate (100 mg) and 2-aminoethylbenzaldehyde hydrochloride (M0748) (390 mg, 2.1 mmol, 2.1 equiv) are added and this mixture is refluxed for 6 h. The reaction mixture is allowed to cool to room temperature, filtered, evaporated to dryness and the crude product purified by column chromatography (gradient CH$_2$Cl$_2$ to 7:3 CH$_2$Cl$_2$:MeOH). Fractions containing the pure aldehyde derivative are combined and recrystallized from toluene.

A sample of the resulting aldehyde (50 mg, 120 µmol) is dissolved in methanol (2 mL). Triisopropylsulfonyl hydrazide (36 mg, 120 µmol) is added and this reaction mixture allowed to stir at room temperature under dry N$_{2(g)}$ overnight. The solvent is removed in vacuo and the resulting solids tritrated with diethyl ether (2×5 mL) followed by EtOAc (1×5 mL). The solids are purified on a column of silicagel 60 (2.5×11 cm) using a gradient elution (5% to 50% MeOH in CH$_2$Cl$_2$). Fractions containing the pure fractions are concentrated in vacuo to give the title compound. (M1797: 50 mg, 60%) homogenous by TLC analysis (irrigant=15% MeOH in CH$_2$Cl$_2$).

Example 20

Preparation of a Green Acridine-Based Labeling Reagent

The following compound was prepared:

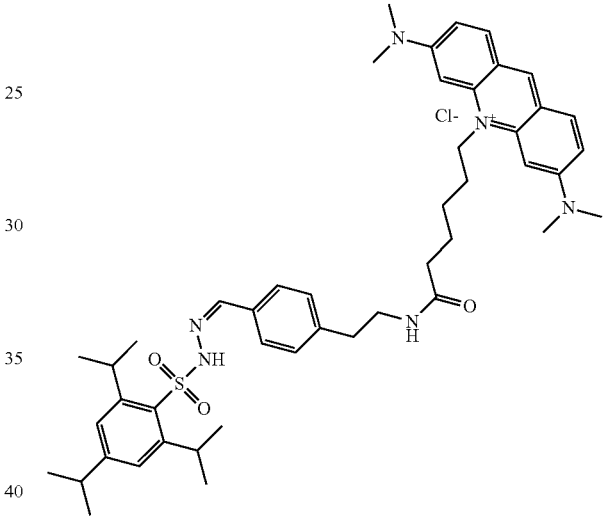

Acridine orange (1.07 g, 4 mmole), 6-bromocaproic acid (975 mg, 5 mmole) and dry toluene (25 mL) were heated to reflux for 15 hours in a dry 100 mL round bottom. After cooling, the solid crude bromide salt was collected by filtration, washed with minimum dry toluene, and dried in vacuo to give a red solid that was recrystallized from hot isopropanol (1.22 grams, 66%).

The resulting carboxylated acridine orange (231 mg, 0.5 mmole) was dissolved in dry DMF (1 mL) and treated with disuccinimidyl carbonate (154 mg, 600 umol) and DMAP (22 mg) and allowed to react for 18 hours at room temperature under anhydrous conditions. TLC analysis showed complete conversion to the succinimidyl ester. The solvent was removed and the residue dissolved in CH$_2$Cl$_2$ (100 mL). The solution was extracted with saturated NaCl (2×100 mL), dried over Na2SO4 and the solvent removed to provide 380 mg crude reactive ester. Reaction of the reactive ester with 4-(2-aminoethyl)benzaldehyde hydrochloride (M0748: 94 mg, 0.5 mmol) and diisopropylethylamine (193 uL, 1.1 mmol) gives the benzaldehyde intermediate which is purified by extraction with CH$_2$Cl$_2$ (100 mL) and saturated sodium bicarbonate solution (2×50 mL); water (1×50 mL) and brine (1×50 mL). The organic layer was dried over anhydrous sodium sulfate, filtered, evaporated and dried in vacuo. The crude product was purified on a column of silicagel 60 (2.5×

23 cm) using a gradient elution (20:1:1 (450 mL), 20:2:1 (210 mL), 20:4:1 (630 mL), 20:8:1 (300 mL), 10:10:1 (200 mL) CH₂Cl₂:MeOH:AcOH). Fractions containing the pure aldehyde are concentrated in vacuo to give a red solid. (M0762: 60 mg, 30%) homogeneous by TLC analysis.

The aldehyde (50 mg, 109 umole) is converted to the corresponding triisopropylsulfonyl hydrazone by treatment with triisopropylsulfonyl hydrazide (36 mg, 120 μmole) in MeOH (5 mL) at room temperature for 15 hours. The solvent is removed, the product triturated with dry diethylether and the solids purified on a column of silicagel 60 (2.5×14 cm) using a gradient elution (0% to 30% MeOH in CH₂Cl₂) to give the title compound (M1800:87 mg, 66%).

Example 21

Preparation of a Blue-Green Diethylaminocoumarin Labeling Reagent

The following compound was prepared:

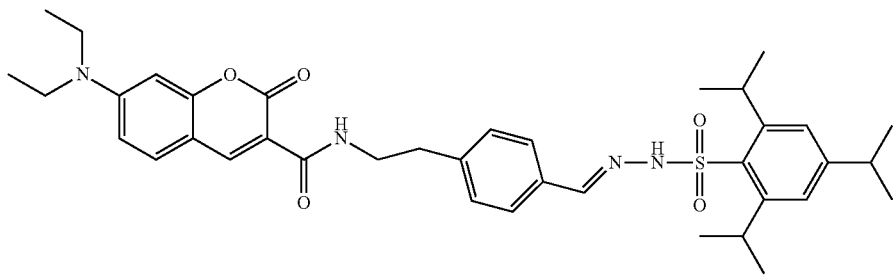 [SMILES: CCN(CC)c1ccc2cc(C(=O)NCCc3ccc(/C=N/NS(=O)(=O)c4c(C(C)C)cc(C(C)C)cc4C(C)C)cc3)c(=O)oc2c1]

To a flame-dried 100 mL round bottom flask was weighed under dry N₂(g) 7-diethylaminocoumarin, 3-carboxylic acid, NHS ester (360 mg, 1.0 mmole). This sample was dissolved in anhydrous DMF (5.0 mL) and 2-aminoethylbenzaldehyde hydrochloride (M0748) (186 mg, 1.0 mmol) added dropwise as a solution in dry DMF (1.0 mL) followed by diisopropylethylamine (436 uL, 2.5 mmole). The flask was flushed with dry N₂(g) and allowed to stir at room temperature under anhydrous conditions overnight. The reaction mixture was diluted with ethylacetate (50 mL) and washed with water (1×50 mL); saturated sodium bicarbonate solution (1×50 mL); water (1×50 mL); saturated brine solution (1×50 mL); and water (1×50 mL). The final organic layer was dried over anhydrous MgSO₄, filtered, evaporated and dried in vacuo (360 mg). This crude sample was purified on a column of Silicagel G (70-230 mesh, 60 A) (50 mL; 120×25 mm) slurry-packed in CH₂Cl₂. The crude sample was applied in CH₂Cl₂ and eluted with 8:2 dichloromethane:ethylacetate as solvent. Fractions containing the pure aldehyde were combined, evaporated and dried in vacuo overnight (300 mg, 77%).

The pure aldehyde (50 mg, 0.127 mmole) was dissolved in anhydrous acetonitrile (7 mL) and triisopropylsulfonylhydrazide (42 mg, 0.140 mmole) added. This solution was allowed to stir at room temperature under dry N₂(g) overnight until TLC analysis showed complete conversion to a new product with higher Rf (0.85; 8:2 DCM:EtOAc). The reaction was concentrated to a low volume and the product crystallized as an amorphous yellow needles (M1723: 49 mg, 68%).

Example 22

Labeling of Oligonucleotides Using the Reactive Labeling Reagents

Labeling of a standard 18-mer telomere oligo sequence 5'-CCCTAACCCTAACCCTAA-3' (SEQ ID NO:1) with the tetramethylrhodamine diazo dye M0776 was carried out at 37° C. for 1 hour. The oligonucleotide was dissolved in nuclease-free water. M0776 was dissolved in dry DMF (5 mM). The final concentration of DMF in labeling mixture was maintained at 20% or less. The labeled products were directly loaded onto 15% Urea-PAGE (Polyacrylamide gel electrophoresis) and visualized under UV transilluminator. Compared with the dye only lane, the labeling mixture lane had a distinct and bright band which migrated at approximate position of an 18-mer oligonucleotide. To further confirm, this PAGE gel was post-stained with 0.5 ug/ml Ethidium Bromide to visualize all DNA bands confirming that the fluorescently labeled band correspond to the 18-mer oligonucleotide. Compared with un-labeled 18-mer oligonucleotide, the labeled sample migrated slightly slower which is consistent with the relative changes in charge for dye labeling of phosphate groups on this oligonucleic acid.

To evaluate the incorporation of dye M0776 into the 18-mer telomere oligonucleotide the dye:oligo molar labeling ratio was varied from 5:1 to 1:1. The labeling reaction was carried out in nuclease-free water with DMF concentration maintained at 10% or lower, 37° C. for 1 hour. Then the labeled oligonucleotides were purified by spin-column purification and analyzed by both by gel-electrophoresis and by spectrometry. Dye incorporation into oligonucleotide was measured by absorbance at 552 nm (excitation wavelength of M0776) and at 260 nm (for DNA). A linear correlation between dye to oligonucleotide ratio and labeling efficiency was observed.

The labeling of a 36-mer oligo (a longer version of telomere oligomer 5'-CCCTAACCCTAACCCTAACCCTAAC-CCTAACCCTAA-3') SEQ ID NO:2 was evaluated using the Cy3 (M1559), Cy5 (M1560) and Fluorescein (M1544) reactive dyes. The labeling reactions were carried out at 37° C. for 1 hour in nuclease-free water with DMF concentration maintained at 20-50% depending on the dye solubility. Dye:oligo molar ratio was maintained at 5:1 in all labeling experiments. The labeled oligonucleotides were purified by column purification and dye incorporation was measured by absorbance spectrometry at the optimum dye absorption wavelength and at 260 nm (DNA). Depending on the properties of the labeling dye, the degree of substitution (DOS) varied as is shown in Table 2.

TABLE 2

Table 2: Degree of substitution (DOS) of TAMRA (M0776), Fluorescein (M1544), Cy3 (M1559) Cy5 (M1560) and Coumarin (M1726)

| | DNA oligomer | Oligo conc (ng/ul) | Oligomer Ext. Coeff (L/mole · cm) | maximum abs | OD | Dye Ext. Coeff | Dye conc. (moles/L) | Oligo conc (mole/L) | DOS (dyes/1000 base) |
|---|---|---|---|---|---|---|---|---|---|
| TAMRA M0776 | 36mer | 289.6 | 329800 | 552 nm | 0.029 | 95000 | 3.0526E−07 | 2.6997E−05 | 11.3 |
| Fluorescein M1544 | 36mer | 266.7 | 329800 | 490 nm | 0.015 | 93000 | 1.6129E−07 | 2.4862E−05 | 6.5 |
| Cy3 M1559 | 36mer | 235.6 | 329800 | 546 nm | 0.319 | 130000 | 2.4538E−06 | 2.1963E−05 | 111.7 |
| Cy5 M1560 | 36mer | 171.5 | 329800 | 651 nm | 0.003 | 150000 | 0.00000002 | 1.5988E−05 | 1.3 |
| Coumarin M1726 | 36mer | 170 | 329800 | 423 nm | 0.071 | 57000 | 1.2456E−06 | 1.5848E−05 | 78.6 |

Labeling of a 36-mer oligo (5'-CCTAACCCTAAC-CCTAACCCTAACCCTAACCCTAA-3') SEQ ID NO:2 using the Biotin labeling dye (M0789) was performed at 37° C. for 1 hour. DMF concentration was kept at 50% in nuclease-free water during the labeling reaction due to lower solubility of Biotin dye (M0789). This labeling mixture was directly loaded onto 15% Urea-PAGE (Polyacrylamide gel electrophoresis) followed by staining with 0.5 ug/ml Ethidium Bromide. Biotin-X (M0789) labeled 36-mer migrated slightly slower than the unlabeled oligomer indicating the incorporation of dye. Alternatively, the Biotin labeled 36-mer was purified by spin column, incubated with streptavidin and then loaded onto 15% Urea-PAGE. The addition of streptavidin caused a supershift of the Biotin labeled 36-mer, confirming the incorporation of Biotin moiety into the oligomer.

Example 23

Labeling of single stranded DNA (ssDNA)

One microgram of salmon testes single-strand DNA (Sigma D9156) was denatured at 95° C. for 5 minutes before incubation with five micrograms of the active tetramethyl-rhodamine diazo dye M0776 at 80° C. for 15 minutes. The ssDNA was dissolved in nuclease-free water and M0776 was in dissolved in dry DMF (5 mM). The final concentration of DMF in labeling mixture was maintained at 20% or less. The labeled products were directly applied to 1% agarose gel electrophoresis and visualized under UV transilluminator. Compared with the dye only lane, the labeling mixture had a distinct and bright smear of DNA ranging from 100-500 bp which is within the normal range of salmon testes ssDNA (100-800 bp). Ethidium Bromide staining confirmed this smear was indeed labeled salmon DNA. The labeling can also be carried out at 37° C. for 1 hr. However, the range of resulting labeled DNA bands was wider than labeled at high temperature (80° C. for 15 minutes).

Labeling of salmon ssDNA using the reactive dyes fluorescein (M1544), dansyl (M1520) and Cy3 (M1559) was also examined. In all cases we were able to observe the fluorescence of labeled ssDNA using the UV transilluminator, albeit slightly dim due to non-optimal excitation wavelength.

To evaluate the stability of reactive labeling dye generated by "method 1"—incubating with an excess of polymer-bound sodium 4-benzyloxybenzyl alkoxide (M1514), salmon ssDNA was labeled with M0776 which had been stored in freezer for 1, 2 and 3 weeks. We were able to demonstrate that M0776 generated by "method 1" and stored at or lower than −20° C. for more than 3 weeks was still viable and able to label nucleic acid efficiently.

Example 24

Labeling of double stranded DNA (dsDNA)

pSV40β Mammalian lacZ Expression Vector (M0952) was digested with NotI plus EcoRI. This digestion generated three bands: 1.0 kb, 2.5 kb and 4.0 kb. The digestion products were purified by spin column and eluted in 20 mM Tris buffer (pH8.0). Two microgram of the dsDNA mixture was incubated with equal amount of reactive dye (M0776) at 37° C. for 1 hour and then applied to 1% agarose gel electrophoresis. Labeled dsDNA bands were visualized under UV illuminator while no fluorescence observed in un-labeled lanes. Staining with 0.5 ug/ml Ethidium Bromide confirmed the DNA bands as well as revealed slight migration difference of labeled dsDNA bands versus un-labeled ones.

Example 25

Centromeric Probe Labeled with the Reactive Dyes were Able to Visualize Centromeres in Chromosome Fluorescence In Situ Hybridization (FISH)

Plasmid pAlpha12H8 containing chromosome 12 specific alpha satellite sequences within the centromeric region was obtained from ATCC (#61398). The 1.35 kb insert in which the satellite sequences resides were excised out with restriction enzyme double digestion using HindIII and SacI, followed by spin column purification. The insert was labeled with the reactive labeling dyes Cy3 (M1559), TAMRA (M0776) and Fluorescein (M1544). The labeled inserts were further purified by ethanol precipitation and resuspended in 20 mM Tris-HCl (pH 8.0). These labeled inserts was used as centromeric probes to visualize centromeric region of chromosome 12 in metaphase chromosome spread analysis by Fluorescence In Situ Hybridization (FISH).

Human breast cancer cell line MDA cells were treated with Colcemid and fixed with Methanol/glacial acetic acid (3/1) until a "milky" suspension formed. Then this cell suspension was spread onto a glass slide, washed with fixing solution and air dried. Observation of the slides under microscopic examination located the spread chromosomes. Slides with 10-15% of spread chromosomes were used for Fluorescence In Situ Hybridization (FISH) analysis with labeled the centromeric probes.

Slides with metaphase chromosome spreads were first treated with RNase digestion, followed by 2×SSC, a series of ethanol washes and then allowed to air dry. The slides were then denatured in 70% formamide in 2×SSC pH 7-7.5 at 72° C. for 3 minutes, followed by a series of ethanol washes and air drying steps. In the meantime, 30 ng of a labeled probe was mixed with 1.2 ug human Cot-1 DNA and 18 ug sheared salmon testes DNA. This mixture was then denatured, neutralized and ethanol precipitated. The precipitate was resuspended in 15 ul of hybridization buffer (50% formamide, 0.1 mg/ml Dextran Sulfate in 2×SSC) and incubated at 75° C. for 10 minutes. This denatured probe is sufficient to cover a 22×22 mm$^2$ area of the slide which was then covered by a similar size glass cover slip. The hybridization was carried out in a humidified hybridization chamber at 42° C. for 16-24 hours in dark. Hybridized slides were then washed three times with 50% formamide in 2×SSC at 45° C. for 5 minutes, washed three times with 0.1×SSC at 45° C. for 5 minutes, one time in 4×SSC/0.1% Tween-20 for 1 min. and finally washed with water for 1 min. Now the slides were ready to be mounted with anti-fade I mounting media (1 mg/ml 1,4-phenylene-diamine, and 77% glycerol in PBS) supplemented with 0.1 ug/ml DAPI. We observed bright dots in the centromeric regions of Chromosome 12. Weak signals in the centromeric regions of other chromosomes were also observed due to slight non-specific cross hybridization.

To visualize the centromeres of all chromosomes during metaphase, a pan-centromeric probe was generated. A pair of degenerate primers (WA1: 5'-GAAGCTTA(A/T)(C/G)T(C/A)ACAGAGTT(G/T)AA-3'; SEQ ID NO:3 WA2: 5'-GCTG-CAGATC(A/C)C(A/C)AAG(A/T/C)AGTTTC-3') SEQ ID NO:4 was used to amplify satellite sequences of centromeric regions of all chromosomes from MDA genomic DNA. The product obtained was 175 bp plus multiples of 171 bp (Weier, et al., 1991). This PCR product was purified by spin column and labeled with reactive labeling dyes Cy3 (M1559) and TAMRA (M0776) as well as with the Biotin-X (M0787) probe.

Fluorescence-labeled pan-centromeric probes were further applied to hybridization assays with metaphase chromosomes in FISH analysis as described previously. We observed bright dots in the centromeric regions of most of the chromosomes, some weak signals in a few chromosomes. This could be due to the fact that the satellite sequences in the centromeric regions of these few chromosomes were not abundantly present in the amplified PCR product.

To confirm the biotin labeling of this pan-centromeric probe, the labeled probe was incubated with streptavidin for 15 minutes before applied to agarose gel electrophoresis. Compared to the un-labeled probe, streptavidin caused a supershift which suggested the efficient biotin incorporation into the probe. Furthermore, this biotin labeled probe was used to hybridize with metaphase chromosomes FISH. To detect this hybridization, a further incubation with fluorescent F405 conjugated streptavidin was undertaken followed by extensive wash of PBS to get rid of free F405-streptavidin. The slides were then mounted in anti-fade mounting media supplemented with propidium iodide. Under fluorescence microscope, we were able to identify blue dots in the centromeric area of the metaphase chromosomes. These specific blue dots were not present in slides which were not further incubated with F405-streptavidin or slides hybridized with non-labeled probe, indicating efficient labeling of centromeric regions.

Example 26

Labeling of Amplified RNA

Mouse K. balb and NIH3T3 fibroblasts were cultured to 70-80% confluence and then treated with 1 ug/ml Resveratrol overnight. The next day, cells were lysed and total RNA extracted using RNeasy mini kit (Qiagen). Then mRNA was reverse transcribed to cDNA with T7 oligo(dT) primer. Second strand of cDNA was then synthesized with DNA polymerase and RNase H. The duplex cDNA was column purified and then was used as a template to in vitro amplify RNA. The generated RNA is complementary to the original mRNA isolated from the cells, thus called anti-sense RNA or aRNA. This amplified aRNA was column purified and used to test the labeling with our reactive dyes.

One microgram of aRNA from NIH3T3 cells was denatured at 95° C. for 5 minutes in nuclease-free water and then incubated with 5 microgram of reactive labeling dye TAMRA (M0776). Alternatively, the labeling was carried out at 37° C. for 1 hour. The reaction products were applied to 1% formaldehyde agarose gel electrophoresis and observed under UV transilluminator. Compared with the dye only lane, the labeling mixture had a distinct and bright smear ranging from 500-1500 bp. Further staining with 0.5 ug/ml Ethidium Bromide revealed that compared to the un-labeled, the labeled aRNA migrate slightly faster. This abnormal migration pattern was not observed if we reduce the amount of reactive labeling dye in the reaction.

One microgram of aRNA from NIH3T3 cells was incubated with 5 ug, 1 ug and 0.2 ug of reactive TAMRA dye (M0776) at 37° C. for 1 hour followed by ethanol precipitation and resuspension in nuclease-free water. The RNA concentration and incorporation of TAMRA was measured with absorbance spectrometry. We observed that the higher the dye/aRNA ratio, the higher the incorporation of dye.

Example 27

Differential Microarray Analysis of aRNA from NIH3T3 Cells with an Affymetrix Microarray System Five micrograms of aRNA from NIH3T3 was mixed with reactive labeling dye Cy3 (M1559) at 10 ug, 2.5 ug and 1 ug respectively. The labeling was carried out at 37° C. for 1 hour. Labeled aRNA was purified by ethanol precipitation and resuspended in nuclease-free water. As observed earlier, the higher the dye/RNA ratio used for labeling, the higher the incorporation. The incorporation of Cy3 was measured by absorbance spectrometry and expressed as pmol per ug of RNA. Representative data is shown in Table 1.

TABLE 1

Incorporation of CY3 dye labeling Degree of Substitution (DOS) as a function of RNA.

| | dye/RNA ratio | | |
|---|---|---|---|
| | 2:1 | 1:2 | 1:5 |
| dye incorporated pmol/ug | 57 | 23 | 10 |

825 ng of Cy3 labeled aRNA was mixed with equal amount of Cy5 labeled control probe, bring the total volume to 41.8 µl with nuclease-free water. 11 µl of 10× blocking agent, 2.2 µl of 25× fragmentation buffer was added and mixed well. This solution was incubated at 60° C. for 30 minutes in the dark to fragment aRNA and improve hybridization efficiency. Then 55 µl of 2× Hi-RPM hybridization buffer was added to stop the fragmentation and the mixture was applied to microarray slide in a hybridization chamber. Let hybridize at 65° C. for 17 hours. The next day, the microarray slide was washed with wash buffer 1 and pre-warmed wash buffer 2, followed by acetonitrile wash to dry the slide. The dried slide was scanned using an Agilent microarray scanner. We observed hybridization spots on the array with varied intensity. Some of the hybridized dots which were also hybridized by control probe turned out to be housekeeping genes; matrix protein and heat shock protein transcripts. aRNA labeled with dye/RNA ratio at 2:1 produced a higher background compared to the other two labeling ratios. Dye/RNA ratio at 1:5 has the lowest background but the hybridization signal was also relatively lower. From this data it appeared that a dye/RNA ratio at 1:2 was optimal for microarray analysis using the Agilent system.

In addition, we also evaluated the hybridization of Biotin (M0787) labeled aRNA using a MOE 430 2.0 Affymetrix microarray system. Twenty microgram of aRNA isolated from NIH3T3 cells was incubated with equal amount of Biotin labeling dye (M0787) keeping the DMF concentration at 50%. The labeling was carried out at 37° C. for 1 hour followed by ethanol precipitation to get rid of un-incorporated free dye. As a comparison, the same amount of aRNA was labeled using the Affymetrix GeneChip 3'-IVT-express kit. To confirm the labeling, both labeled aRNA were incubated with streptavidin for 15 minutes and applied to 1% agarose gel electrophoresis. Streptavidin caused a supershift of both labeled aRNA samples, suggesting excellent incorporation of the Biotin moiety in the aRNA.

The biotin labeled aRNAs were fragmented at 94° C. for 35 minutes and then hybridized to MOE 430 2.0 arrays according to standard procedures. Hybridized arrays were stringently washed and hybridized signals were amplified. The arrays were then scanned and positive signals were recorded. The array with M0789 reactive biotin labeled aRNA was compared with the array performed with Affymetrix standard procedures. We found that there was excellent correlation with correlation coefficiency r=0.91.

Example 28

Labeling of cDNA Isolated from Tumor Cell Lines Grown in Culture

Murine D5 (melanoma), 4T1 (breast tumor), and NIH3T3 (fibroblast) cell lines were routinely cultured with RPMI media supplemented with 10% calf serum (37° C., humidified 10% $CO_2$). Cells were treated with or without 1 ug/ml resveratrol overnight, and then lysed. Total cellular RNAs were isolated using an RNA prep columns and poly (A+) mRNA selected using the PolyATtract Kit (Promega). cDNA was synthesized by reverse transcription from total isolated mRNA (Toole, et al., 1984) using an oligo-dT primer (21mer) employing SuperScript II reverse transcriptase (Gibco BRL). The generated cDNAs were labeled with reactive TAMRA labeling dye (M0776) for 2-3 hours at room temperature. The labeled product was then applied to 1% agarose gel electrophoresis and observed under UV transilluminator. A fluorescent streak of DNA was observed spanning the range of cDNA, which was further confirmed with ethidium bromide staining.

Example 29

Differential Microarray Analysis of cDNA Isolated from Murine Cell Lines with or without Treatment of Several Cytotoxic Drugs Murine fibroblasts, K. balb and NIH3T3 cells, were cultured with or without treatment with several cytotoxic drugs including 5-fluorouridine, resveratrol and anisomycin. After incubation for 24-72 hours, total RNA was isolated using RNeasy mini kit (Qiagen) or similar method. Anti-sense RNA (aRNA) was transcribed in vitro from the total RNA isolated using MessageAMP aRNA kit (Ambion) or equivalent. cDNA was synthesized by M-MuLV reverse transcriptase (First Strand cDNA Synthesis Kit, Fermentas) from the amplified aRNA. After denaturing at 70° C. for 5 min., the aRNA (5 µg), oligo(dT)$_{18}$ primer (3 µL of 0.5 µg/µL), dNTP (64 µL of 10 mM), and enzyme (6 µL of 20 u/µL) were reverse transcribed for 2 hours at 37° C. cDNA (~5 µg) was labeled (3 hours at 25° C.) with excess reactive labeling dye M0776 (2.5 µL of 10 µg/µL of DMSO). The labeled cDNA was purified by QIAprep spin column (Qiagen) or equivalent. The purified labeled cDNA samples were quantified by UV spectrometry and analyzed using microarray assay system (Perkin-Elmer ScenArray 4000XL) using an SMCmou8400A mouse array printed from the NIH-NIA 15K library. A distinct pattern of hybridization was observed on the array with different murine cell lines. Cytotoxic drug treatment selectively increased or decreased the expression of certain genes. Again this gene pattern change was also distinct with each cytotoxic drug.

M0776-labeled cDNA prepared from the murine fibroblasts was also qualitatively compared with cDNA samples obtained by labeling using a biotin-deoxynucleotide triphosphate and a reverse transcription (RT) reaction employing SuperScript II reverse transcriptase (Gibco BRL), followed by fluorescently-labeled streptavidin conjugation. When tested in comparison with 5'-phosphate diazo-fluorophore labels for sequence dependence of labeling intensity and for hybridization efficiency, the direct labeling techniques were found not only to have comparable or superior intensity but also exhibited improved photostability compared to conventional Cy5 derivatization, under multiple analyses of the same array (approx. 50% reduction in fluorescence intensity noticed for Cy5 labeled array, approx 95% retention of fluorescence intensity observed for M0776 labeled array; 2 scans).

Example 30

Labeling Reagents can be Used to Covalently Attach to DNA Probes for Use in Identifying DNA in Gels (Southern/Northern Blot Analysis)

pSV40β Mammalian lacZ Expression Vector (M0952) is digested with XhoI plus EcoRV. This digestion generates two bands: 1.5 kb and 5.5 kb. The 1.5 kb band, which contains LacZ fragment, is excised, purified by spin column and eluted in nuclease-free water. This purified fragment is further labeled with activated biotin reactive dye (M0787) at 37° C. for 1 hour, ethanol precipitated and re-suspend in 20 mM Tris buffer (pH8.0). This labeled LacZ fragment will be used as probe for northern or southern blot.

pSV40β Mammalian lacZ Expression Vector (M0952) is again digested with NotI plus EcoRI. This digestion generates three bands: 1.0 kb, 2.5 kb and 4.0 kb. Only the 2.5 kb band contains the LacZ gene. The digestion products are applied to agarose gel electrophoresis and then transferred to nylon membrane. The membrane is pre-hybridized with pre-hybridization buffer (6×SSC, 5×Denhardt's, 0.5% SDS, 100 □g/ml denatured and fragmented salmon testes DNA, 50% formamide) at 42° C. for 1-2 hours. The biotin labeled LacZ probe is denatured with NaOH and renatured by HCl, and add to the pre-hybridization buffer to a concentration of 10 ng/ml. Then the membrane is hybridized overnight at 42° C. Hybridized membrane is stringently washed with 0.1×SSC and 0.5%

SDS at 68° C. for 15 minutes. Repeat the wash for additional two times. Then the membrane is rinsed with 0.1×SSC at room temperature, incubate with HRP conjugated streptavidin and develop with chemiluminescence reagent to visualize the hybridized band. Only the 2.5 kb band will hybridize to the LacZ probe.

mRNA is extracted from LacZ-expressing murine fibroblast Crebag2 and applied to 1% formaldehyde agarose electrophoresis gel. The separated mRNA is transferred to a nylon membrane and immobilized by a UV crosslinking. The membrane is pre-hybridized with pre-hybridization buffer (6×SSC, 5×Denhardt's, 0.5% SDS, 100 µg/ml denatured and fragmented salmon testes DNA, 50% formamide) at 42° C. for 1-2 hours. The biotin labeled LacZ probe is denatured with NaOH and renatured by HCl, and add to the pre-hybridization buffer to a concentration of 10 ng/ml. The membrane is then hybridized overnight at 42° C. The hybridized membrane is stringently washed three times with 0.1×SSC and 0.5% SDS at 68° C. for 15 minutes each. Then the membrane is rinsed with 0.1×SSC at room temperature, incubated with horse radish peroxidase (HRP) conjugated streptavidin and developed with luminol chemiluminescence reagent to visualize the hybridized band (Immobilon, Millipore or equivalent system). The band correspond to LacZ mRNA exhibits a distinct hybridized photo band by X-ray film detection (Fuji HR-L/HA 30 or equivalent).

Example 31

Labeling of Nucleotides and Deoxynucleotides

Solutions of 2'-Deoxyguanosine 5'-monophosphate sodium salt hydrate (dGMP) (1 mM) and Adenosine 5'-monophosphate disodium salt (AMP) (1 mM) in water (50 uL each), were labeled with reactive labeling dyes Cy3 (M1559) and TAMRA (M0776) as well as with the Biotin-X (M0787) probe (50 uL, 5 mM solutions; 1 hour, room temperature). The reaction mixtures were analyzed by Merck Kieselgel 60 $F_{254}$ silicagel TLC analysis (irrigant=18:2:1 $CH_2Cl_2$:MeOH:TEA). In each case, the labeled nucleotide or deoxynucleotide migrated with a higher Rf value compared with the native nucleotide or deoxynucleotide.

Example 32

Labeling of miRNA and Microarray Analysis

Regulation of micro RNA (miRNA) expression plays a significant role in many biological processes. Array analysis currently remains to be the major method to evaluate their expression in cells/tissues. Total RNA including miRNA was extracted from cultured NIH3T3 cells and labeled with biotin reagent M0789. Excess label was removed and the labeled miRNA was column purified. Successful labeling was confirmed by incubating the labeled miRNA with 4-fold excess streptavidin. A supershift of the band revealed by gel electrophoresis indicated the incorporation of biotin (FIG. 1). The same RNA was also labeled using the Genisphere 3DNA FlashTag Biotin labeling kit performed according to the manufacturer's procedures. The same amount of both labeled miRNA samples were applied to Affymetrix mouse miRNA array chips for hybridization. As set forth in Table 3, hybridized miRNA with OliGlo™ M0789 biotin labeling reagent exhibited more positive hits of compared to the Genisphere 3DNA FlashTag Biotin labeling (7321 vs 6998). Further analysis revealed that the hits identified in arrays with the two labeling method only had 68% correlation. Several labs have reported the biased labeling with enzyme-based labeling method. Statistical analysis showed that a bias in the labeling with adenine or uracil at the 3' end base was significantly higher in the Genisphere enzyme-based method using versus the OliGlo™ system. In addition, certain hairpin sequences also exhibited biased labeling in the enzyme-based labeling system compared to the OliGlo™ methods (see FIG. 1)

TABLE 3

Summary of intensities and hits from miRNA array analysis

| Filenames | Mean Intensity | Mean Background Intensity | Number of Probes | Number of Detected Probes |
|---|---|---|---|---|
| Flash Tag | 835.13 | 116.72 | 45930 | 6998 |
| OliGlo ™ | 598.21 | 151.89 | 45930 | 7321 |

Example 33

Labeling of mRNA and Direct Analysis in Fixed Cells

To visualize mRNA in situ of cells/tissue sections, a fluorophore or biotin labeled DNA oligonucleotide set or cDNA fragments are used to hybridize with expressed mRNA inside cells or tissues. Labeled oligonucleotide probes were used to visualize lacZ mRNA in CREBAG2 embryonic mouse fibroblast cells, which is a lacZ stably transfected mouse fibroblast cell. The lacZ targeting oligo (5'-TGTAAAACGACGGC-CAGT-3') SEQ ID NO:5 was labeled with the M0789 OliGlo™ biotin labeling reagent, ethanol precipitated and resuspended in 10 mM Tris pH8.5. Incorporation of biotin was verified by gel supershift after incubating with Streptavidin (FIG. 2). This probe can be stored at −20° C. for several weeks.

CREBAG2 murine embryonic fibroblast cells were grown on a sterile coverslips and incubated at 37° C., in a 5% $CO_2$ atmosphere overnight. The next day, the cells were fixed with 3.7% formaldehyde in PBS for 15 minutes followed by brief washes (2×) in 2×SSC salt solution. Then cells were acetylated with 0.25% acetic anhydride in 0.1M triethanolamine (pH8.0) for 10 min and washed using both 1×SSC and 10×PBS buffers. Samples were then incubated in 0.2M Tris/0.1M glycine (pH7.5), rinsed with 2×SSC, dehydrated in a series of ethanol solutions and air dried. The treated coverslips were pre-hybridized in a buffer containing 25% formamide, 6×SSC, 5×Denhardt's solution and 500 µg/ml salmon sperm DNA at 42° C. for 1 hour in a humid chamber. Hybridization was performed in a pre-hybridization buffer with a 10 µg/ml sample of the biotin-labeled lacZ probe prepared as described above, at 42° C. overnight. Hybridized coverslips were washed in 2×SSC and 0.1×SSC salt solution and then applied for detection. Biotinylated probe were detected in two ways: 1) Biotin/R-phycoerythrin conjugated Streptavidin (SAPE) amplification; 2) alkaline phosphatase conjugated Streptavidin and subsequent incubation with a precipitating fluorescent phosphatase substrate. For Biotin/SAPE detection, washed coverslips were incubated with 5 µg/ml SAPE in blocking solution (3% BSA in 4×SSC, 0.05% TritonX-100) for 30 minutes at room temperature, washed in washing buffer (4×SSC, 0.05% TritonX-100), then incubated with 10 µg/ml Biotinylated anti-streptavidin in blocking buffer for 30 minutes. After washing, the coverslips were again incubated with 5 µg/ml SAPE in blocking solution for 30 minutes, washed and dehydrated in a series of ethanol solutions and air dried. Each coverslip was then mounted with anti-fade mounting medium supplemented with DAPI, and observed under fluorescence microscope detection with appropriate filter sets for both DAPI and PE detection.

For detection with AP-Streptavidin/phosphatase substrate, washed coverslips were blocked with an mRNA blocking buffer for 1 hour and incubated with 10 µg/ml AP-Streptavidin in blocking buffer for 30 minutes. Samples were then washed with a mRNA wash buffer, equilibrated into developing buffer, and incubated with a precipitating fluorescent phosphatase substrate for 1 hour at room temperature. Then the coverslips were co-stained with 2 µg/ml Hoechst 33342, mounted onto slides with mounting medium and observed by epifluorescence microscopy using appropriate filters for both the green precipitating dye and Hoechst staining. Bright and specific mRNA signals were detected in the cytosol of CRE-BAG2 cells while only background signals were observed if no biotinylated lacZ probe was not included in the hybridization cocktail (see FIG. 2 for representative data).

In addition to oligonucleotides, a cRNA as well as a cDNA fragments can also be used as probes for mRNA in situ hybridization. Additional steps were required if cDNA fragments are for labeling and detection used since denaturation and separation of the double-strand nucleotides are needed before applying to samples for hybridization.

The above examples of labeling reagents represent a diversity of structure and functional types for comparative analysis. New methods for the synthesis of carboxytetramethyl-rhodamine, rhodamine 110, carbocyanine, NBD and DANSYL derivatives are described herein. Other reactive labeling agents were prepared by a similar methodology. Use of the protected hydrazine reagent 2,4,6-triisopropylphenyl-sulfonyl hydrazide, followed by deblocking, consistently gave higher yields of the final reactive dyes, than using hydrazine, manganese dioxide directly. In addition, use of a p-nitrophenyl or o-nitrophenylsulfonyl hydrazide followed by deblocking using a milder thiol containing polymer, could be used to activate the labeling reagents. Each of the final protected hydrazide reactive dye reagents were fully characterized, by $^1$H-n.m.r., thin-layer chromatography, UV and fluorescence spectrometry, as well as labeling, HPLC and fluorescence measurements by standard reaction with AMP. Each of the products was determined to be of approximately 90-99% purity by these analyses. Solutions of these reactive dyes in anhydrous dimethylformamide (DMF) or dimethyl-sulfoxide (DMSO) solution were found to be stable without decomposition for up to several months after manufacture ($T_{1/2}$~3 mo.) if stored at −20° C., desiccated (t.l.c. analysis).

What is claimed is:

1. A method for direct labeling of an analyte comprising:

a. contacting a protected labeling compound with a polymer-based activating reagent having a polymer-bound moiety in a reaction mixture to generate a reactive labeling compound having a different density from said protected labeling compound and said activating reagent;

b. separating said reactive labeling compound from said reaction mixture;

c. contacting said reactive labeling compound with an analyte having a nucleophilic group capable of reacting with said reactive labeling compound;

wherein the protected labeling compound comprises the structure:

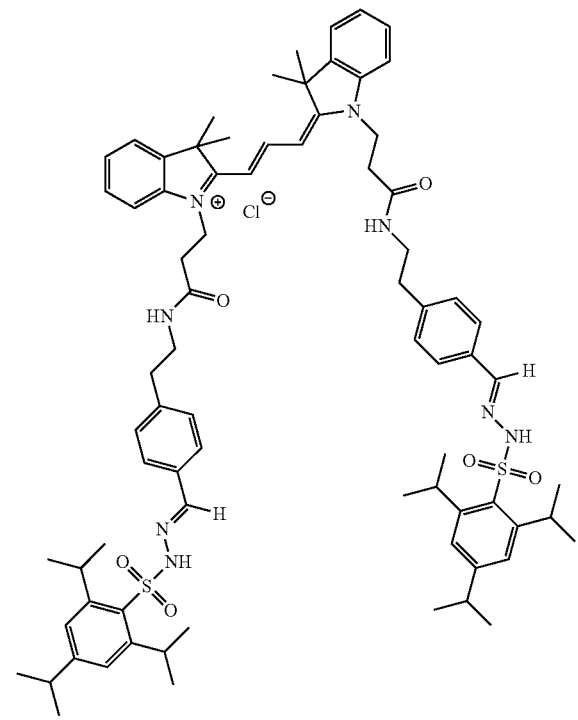 [SMILES: CC(C)c1cc(C(C)C)c(S(=O)(=O)N/N=C/c2ccc(CCNC(=O)CCN3/C(=C/C=C/C4=[N+](CCC(=O)NCCc5ccc(/C=N/NS(=O)(=O)c6c(C(C)C)cc(C(C)C)cc6C(C)C)cc5)c5ccccc5C4(C)C)C(C)(C)c4ccccc43)cc2)c(C(C)C)c1 ; [Cl-]]

* * * * *

SEQUENCE LISTING

<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: Probe

<400> SEQUENCE: 1
ccctaaccct aaccctaa                                                 18

<210> SEQ ID NO 2
<211> LENGTH: 36
<212> TYPE: DNA
<213> ORGANISM: Artificial Sequence
<220> FEATURE:
<223> OTHER INFORMATION: Probe

<400> SEQUENCE: 2
ccctaaccct aaccctaacc ctaaccctaa ccctaa                             36

<210> SEQ ID NO 3
<211> LENGTH: 23
<212> TYPE: DNA
<213> ORGANISM: Artificial Sequence
<220> FEATURE:
<223> OTHER INFORMATION: Probe

<400> SEQUENCE: 3
gaagcttaws tmacagagtt kaa                                           23

```
<210> SEQ ID NO 4
<211> LENGTH: 23
<212> TYPE: DNA
<213> ORGANISM: Artificial Sequence
<220> FEATURE:
<223> OTHER INFORMATION: Probe

<400> SEQUENCE: 4
gctgcagatc mcmaaghagt ttc                                          23

<210> SEQ ID NO 5
<211> LENGTH: 18
<212> TYPE: DNA
<213> ORGANISM: Artificial Sequence
<220> FEATURE:
<223> OTHER INFORMATION: Probe

<400> SEQUENCE: 5
tgtaaaacga cggccagt                                                18
```